US006371950B1

United States Patent
Roslansky et al.

(10) Patent No.: US 6,371,950 B1
(45) Date of Patent: Apr. 16, 2002

(54) INCONTINENCE ARTICLE FOR MALES

(75) Inventors: Apiromraj Srisopark Roslansky, Boulder, CO (US); Gregory James Hess, Fremont; Kenneth Raymond Schueler, Jr., Appleton, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/160,018

(22) Filed: Sep. 24, 1998

Related U.S. Application Data

(60) Provisional application No. 60/070,048, filed on Dec. 30, 1997.

(51) Int. Cl.[7] .............................................. A61F 13/15
(52) U.S. Cl. ........................... 604/385.19; 604/385.01; 604/385.27; 604/385.28
(58) Field of Search ..................... 604/385.01, 385.19, 604/385.27, 385.28, 385.24, 385.25, 385.26

(56) References Cited

U.S. PATENT DOCUMENTS

| 3,901,236 A | 8/1975 | Assarsson et al. ........... 128/284 |
| 4,076,663 A | 2/1978 | Masuda et al. ...... 260/17.4 GC |
| 4,286,082 A | 8/1981 | Tsubakimoto et al. ...... 526/240 |
| 4,340,563 A | 7/1982 | Appel et al. ................. 264/518 |
| 4,388,075 A | 6/1983 | Mesek et al. ................ 604/385 |
| 4,405,297 A | 9/1983 | Appel et al. ............... 425/72 S |
| B14,699,823 A | 10/1987 | Kellenberger et al. ...... 428/219 |
| 4,704,116 A | 11/1987 | Enloe ....................... 604/385 A |
| 4,846,823 A | 7/1989 | Enloe ....................... 604/385.2 |
| 4,938,754 A | 7/1990 | Mesek ..................... 604/385.2 |
| 5,028,224 A | 7/1991 | Pieper et al. .............. 425/80.1 |
| 5,397,318 A * | 3/1995 | Dreier ..................... 604/385.2 |
| 5,558,659 A * | 9/1996 | Sherrod et al. .......... 604/385.2 |
| 5,562,650 A | 10/1996 | Everett et al. .............. 604/378 |
| B15,147,343 A | 3/1998 | Kellenberger ............... 604/368 |
| 5,810,799 A | 9/1998 | Slater ..................... 604/385.1 |

FOREIGN PATENT DOCUMENTS

GB  2 284 552 A  6/1995

* cited by examiner

Primary Examiner—John G. Weiss
Assistant Examiner—Michael Bogart
(74) Attorney, Agent, or Firm—Patricia A. Charlier; Thomas J. Connelly

(57) ABSTRACT

Absorbent articles of the present invention are specifically adapted for the adult male anatomy. The articles include a moisture barrier, a liner bonded to the moisture barrier, and an absorbent assembly sandwiched therebetween. The moisture barrier is gathered along each of its side edges between forward and rearward terminal points. The moisture barrier is gathered along its back end by an elasticized back pouch member. The back pouch member includes a flange section and a pouch section. The pouch section includes a substantially fixed edge portion, an elasticized gathered movable edge portion, a substantially liquid impermeable pouch barrier layer, a pouch fabric layer, and a plurality of separate laterally extending pouch elastic members sandwiched between the pouch barrier layer and the pouch fabric layer. In particular embodiments, a retaining member is bonded to the liner and defines therebetween a compartment having a volume, and a cover formed of a liquid impermeable material is bonded to the liner.

20 Claims, 9 Drawing Sheets

INCONTINENCE ARTICLE FOR MALES

This application claims priority from U.S. provisional application No. 60/070,048, filed on Dec. 30, 1997.

BACKGROUND OF THE INVENTION

The present invention relates generally to the field of absorbent articles. More particularly, the invention pertains to a disposable absorbent article adapted specifically for use by male wearers, and incorporating a distinctively elasticized barrier or containment system at a waistband portion of the article.

Urine incontinence is a serious concern for many individuals. While the incidence of urine incontinence is greater for females than males, many men as well suffer at one time or another from urine incontinence.

Nevertheless, the majority of incontinence products have not been designed specifically for males. Rather, most incontinence products have been formed similar to conventional diapers, in that they are generally planar, rectangular or hourglass shaped, and sized to receive both urine and feces. Such urine and excrement collecting devices have several disadvantages. In particular, they are designed to handle additional waste than what is necessary for persons who solely require a urine-collecting device. Consequently, such products sacrifice comfort by occupying space between the legs of the wearer and extending up to the small of the back, and as a result such products are often too bulky for discreet protection. The wearer may, simply by sitting, shift the position of the product and/or reduce the absorbent potential of the product.

Urine specific products in the form of pads and guards are commercially available. These products desirably provide discreet incontinence protection in a comfortable fashion. Lacking specific accommodation for the male anatomy, however, these products are more suited for females.

Most male-specific products that have been provided to date have included stocking-shaped sheaths with an insertion opening. Below the opening is a cone-shaped pocket lined with absorbent material. The penis or penis and scrotum of the wearer are inserted through the opening and reside in the pocket. Such sheath devices may present obvious disadvantages. For example, to avoid leakage, the edge portions of the opening often close tightly against the skin in the area around the penis. The result is either a lack of comfort or a risk of leakage. Further, the penis and possibly the scrotum as well are surrounded by absorbent material. This can result in an unpleasant sensation of dampness after urination and skin irritation from exposure to urine.

Conventional absorbent articles, such as disposable male guards, have been constructed with various types of elasticized waistbands and elasticized leg bands or leg cuffs. Such articles have also included additional, elasticized containment or barrier flaps at the leg and/or waist or end sections of the article. Such designs may incorporate a stretchable outer cover composed of an elastomeric web material, such as a stretch-bonded laminate which includes a layer of nonwoven fabric.

Articles which incorporate convention waist flap configurations, however, have exhibited various shortcomings. For example, it has been difficult to maintain the desired operation of the end flaps when the articles are being worn. Even when the end flaps are constructed of an elastomeric material or otherwise elasticized, it has been difficult to maintain contact between the movable edge of the end flap and the wearer's body and has been difficult to reliably hold the flap open for an effective receipt and containment of urine. As a result, there has been a continued need for improved containment structures at the leg and end regions of the absorbent articles.

What is lacking and needed in the art is an absorbent article suitable for use by males that provides a dry environment for the penis and scrotum, addresses the needs of urine-only incontinent individuals, and is shaped so that it is comfortable and discreet to wear and tailored to fit the adult male anatomy.

SUMMARY OF THE INVENTION

In response to the discussed difficulties and problems encountered in the prior art, a new disposable absorbent article has been developed. Absorbent articles of the present invention comfortably contain the male genitalia, reduce leakage and promote dryness. In one embodiment, an absorbent article of the present invention has longitudinal and transverse axes and includes a moisture barrier formed of a liquid impermeable material. The moisture barrier defines a front end, a back end longitudinally spaced from the front end, and a pair of side edges extending between the front and back ends. The moisture barrier has a length measured between the front and back ends of less than about 46 centimeters.

The absorbent article also includes an absorbent assembly and a bodyside liner formed of a liquid permeable material. The bodyside liner is bonded to the moisture barrier to sandwich the absorbent assembly there between. The moisture barrier is gathered along each side edge between forward and rearward terminal points. The forward terminal points are spaced from the front end of the moisture barrier by at least about 7 centimeters, and the rearward terminal points are spaced from the back end of the moisture barrier by less than about 5 centimeters. A pair of elasticized containment flaps are disposed on the liner so that each containment flap extends longitudinally toward the front end to a position at least about 10 centimeters from the back end of the moisture barrier.

The absorbent article is also gathered along its back end. An elasticized back pouch member is connected to at least one of the moisture barrier and the bodyside liner along the back end of the article. The back pouch member includes an extending flange section and an extending pouch section. The pouch section of the back pouch member includes a substantially fixed edge portion secured to the article, and an elasticized, gathered moveable edge portion, which is longitudinally spaced from the fixed edge portion. In particular aspects, the pouch section can also include a substantially liquid impermeable pouch barrier layer, and a fabric layer connected in facing relation with the pouch barrier layer. In other aspects, a plurality of separate, laterally (transversely) extending pouch elastic members can be sandwiched between the pouch barrier layer and the pouch fabric layer to provide an elasticized back pouch composite which is substantially laterally gathered.

The various aspects of the invention can provide a back pouch member structure which can more reliably and more effectively maintain an open position when the associated absorbent article is being worn. In addition, the open pouch configuration can be sustained while avoiding excessive irritation of the wearer's skin. The arrangements of the constituent components and the combination of operational parameters, such as the controlled stiffness and the controlled articulation of the back pouch member, can advantageously provide an improved absorbent structure which can have less leakage, and can afford increased comfort to the wearer.

This design yields a relatively short article that is targeted for urine incontinence. In use, the back end of the article is positioned adjacent the perineum of the wearer so that the wearer generally does not sit on the article. Thus, the absorbent assembly is less subject to bunching and twisting during use. The article is gathered along the sides near the back end and along the back end to form a cupped region in which the scrotum of the wearer resides. Also, the penis of the wearer is maintained over the absorbent assembly by the elastic containment flaps.

In another embodiment, an absorbent article of the present invention generally includes a moisture barrier formed of a liquid impermeable material. The moisture barrier defines a front end, a back end and a pair of side edges, and has a length of from about 18 to about 46 centimeters. A bodyside liner formed of a liquid permeable material is bonded to the moisture barrier to sandwich an absorbent assembly therebetween. A retaining member of the absorbent article is bonded to the bodyside liner and defines therebetween a compartment having a volume of at least about 25 cubic centimeters. An opening to the compartment is located within about 20 centimeters of the back end of the moisture barrier, and the compartment extends from the opening toward the front end at least about 5 centimeters. Longitudinal gathering members are operatively joined to the moisture barrier along each side edge and are longitudinally offset toward the back end of the moisture barrier.

A transverse gathering member is operatively joined to the moisture barrier along its back end. Typically, the transverse gathering member is an elasticized back pouch member connected to the moisture barrier along the back end of the article. The back pouch member includes an extending flange section and an extending pouch section. The pouch section of the back pouch member includes a substantially fixed edge portion secured to the article, and an elasticized, gathered moveable edge portion, which is longitudinally spaced from the fixed edge portion. In particular aspects, the pouch section can also include a substantially liquid impermeable pouch barrier layer, and a fabric layer connected in facing relation with the pouch barrier layer. In other aspects, a plurality of separate, laterally (transversely) extending pouch elastic members can be sandwiched between the pouch barrier layer and the pouch fabric layer to provide an elasticized back pouch composite which is substantially laterally gathered.

In particular embodiments, the absorbent article also includes a cover formed of a liquid impermeable material and bonded to the bodyside liner. The cover has a surface area of at least about 13 square centimeters, is positioned longitudinally between the retaining member and the back end of the moisture barrier, and extends longitudinally inward from the back end by at least about 4 centimeters.

This aspect of the invention provides an especially dry environment for the wearer. The retaining member holds the penis of the wearer in its proper position, while the cover protects against leakage past the back end of the abbreviated article. The penis is held in the compartment with the scrotum resting on the cover.

As can be seen from the foregoing, an absorbent article of the present invention provides urine-only incontinent individuals a dry environment for the penis and scrotum, in a cupped structure that is comfortable and discreet to wear. Articles of the invention can be efficiently manufactured.

Numerous other benefits and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
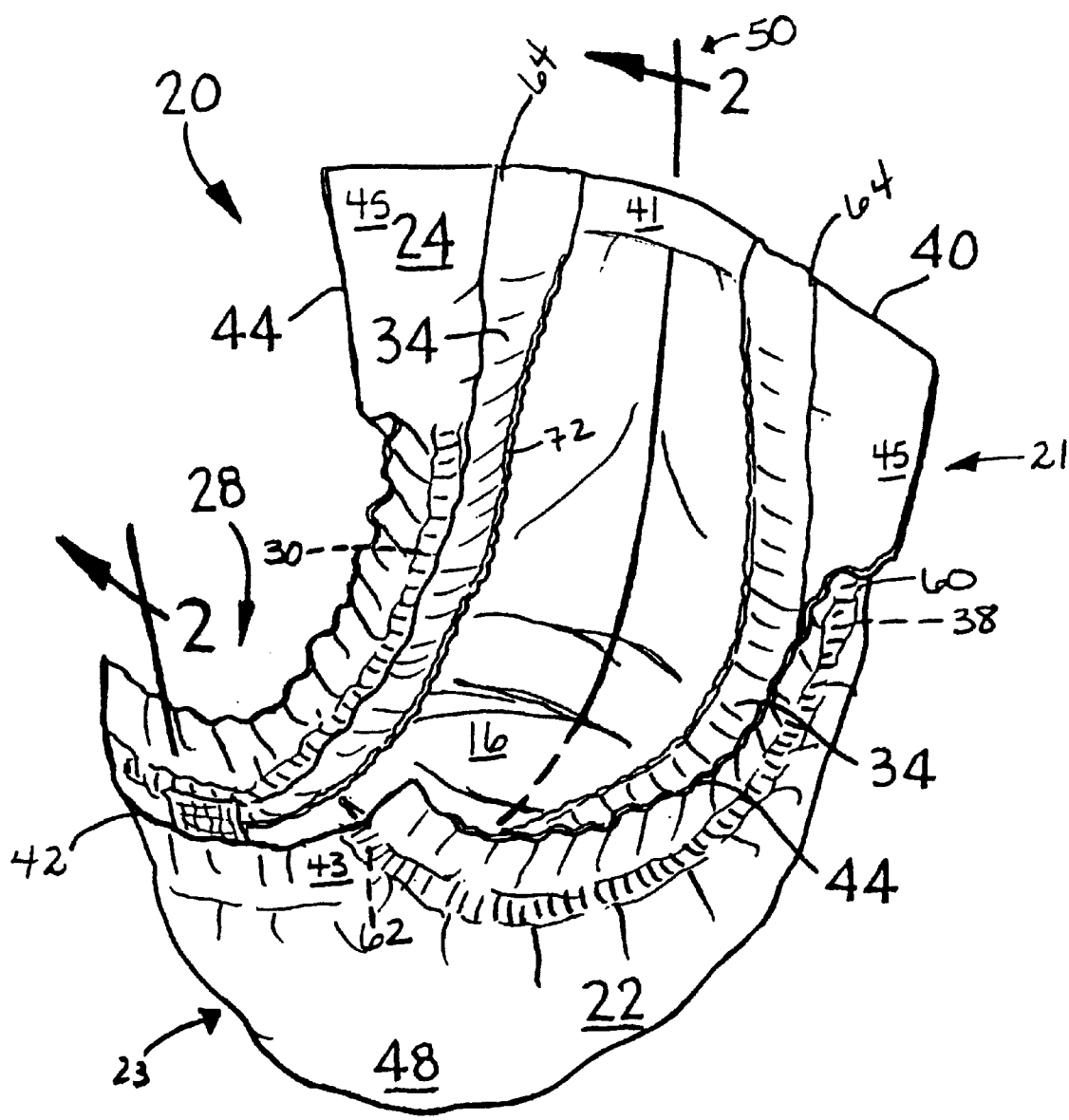
FIG. 1 is a perspective view of a disposable absorbent article according to the present invention.

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed", "disposed on", "disposed with", "disposed at", "disposed near", and variations thereof are intended to mean that one element can be integral with another element, or that one element can be a separate structure joined to or connected to or placed with or placed near another element.

(d) "elastic," "elasticized" and "elasticity" include that property of a material by virtue of which it tends to recover its original size and shape after removal of a force causing the deformation.

(e) "liquid communication" means that liquid is able to pass between the specified layers.

(f) "fabrics" includes all the woven, knitted, and nonwoven fibrous webs.

(g) "force" includes a physical influence exerted by one body on another which produces acceleration of bodies that are free to move and deformation of bodies that are not free to move. Force is expressed in grams per unit area.

(h) "front" and "back" are used to designate relationships relative to the garment itself and not necessarily any position the garment assumes when it is positioned on a wearer.

(i) "gathered" and "gatherable" refer to a material that is or can be drawn together such as in pleats or folds.

(j) "member" when used in the singular can have the dual meaning of a single element or a plurality of elements.

(k) "nonwoven web" means a web of material which is formed without the aid of a textile weaving or knitting process.

(l) "operatively joined", with reference to the attachment of an elastic member to another element, means that the elastic member when attached to or connected to the element, or treated with heat, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(m) "outward" refers to a position relative to the center of an absorbent article, and particularly transversely and/or longitudinally away from the longitudinal and transverse center of the absorbent article.

(n) "stretch bonded" refers to an elastomeric strand being bonded to another member while said elastomeric strand is elongated at least about 25 percent of its relaxed length. Desirably, the term "stretch bonded" refers to the situation wherein the elastomeric strand is elongated at least about 100 percent, more desirably at least about 300 percent, of its relaxed length when it is bonded to the other member.

(o) "stretch bonded laminate" refers to a composite material having at least two layers in which one layer is a gatherable layer and the other layer is an elastic layer. The layers are joined together when the elastic layer is in a stretched condition so that upon relaxing the layers, the gatherable layer is gathered.

(p) "tension" includes a uniaxial force tending to cause the extension of a body or the balancing force within that body resisting the extension.

These definitions are not intended to be limiting, and these terms may be defined with additional language in the remaining portion of the specification.

DETAILED DESCRIPTION OF THE PREFERRED EMBODIMENTS

Figure 2:
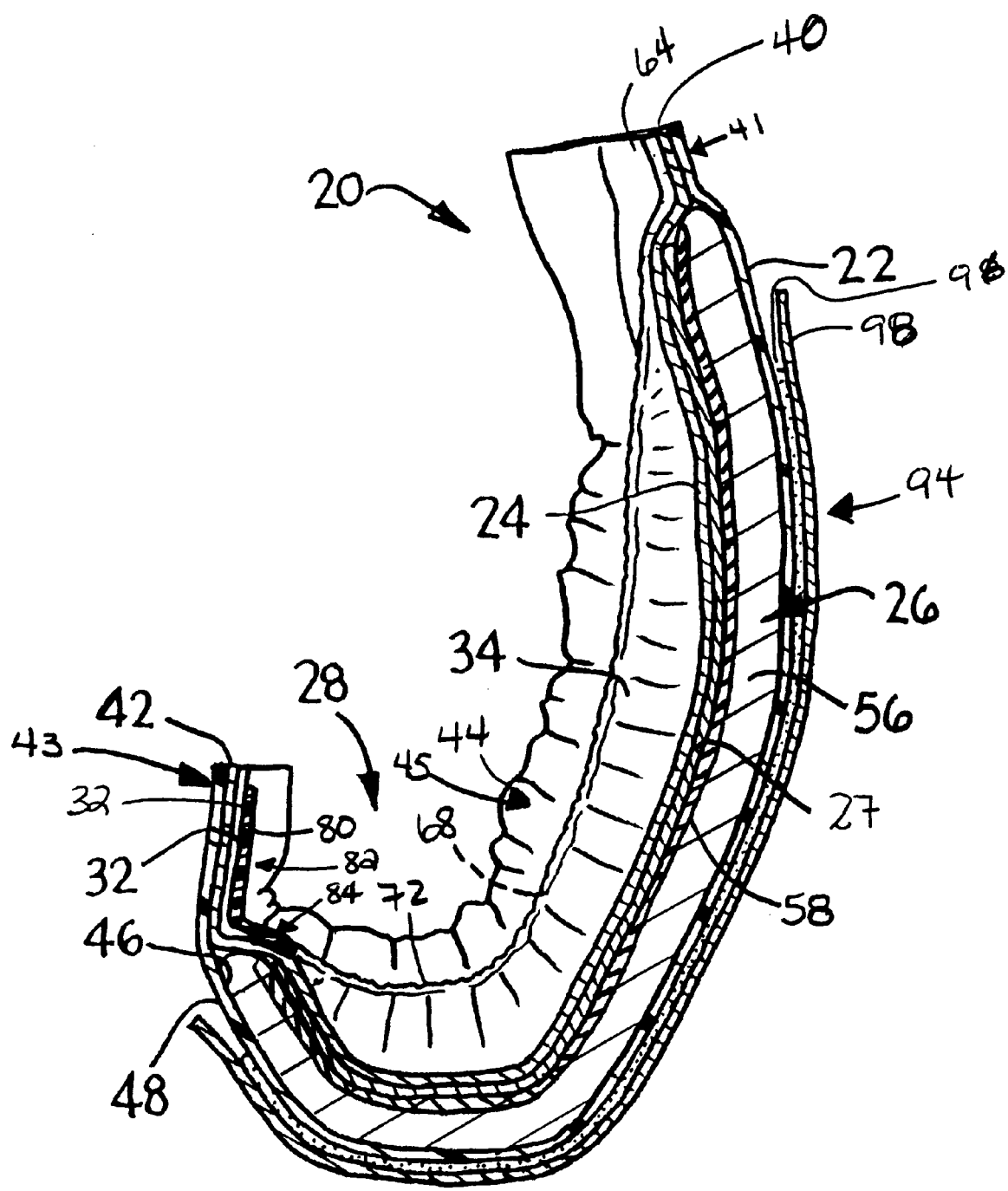
FIG. 2 is an enlarged longitudinal section view taken generally from the plane of the line 2—2 in FIG. 1.
Figure 3:
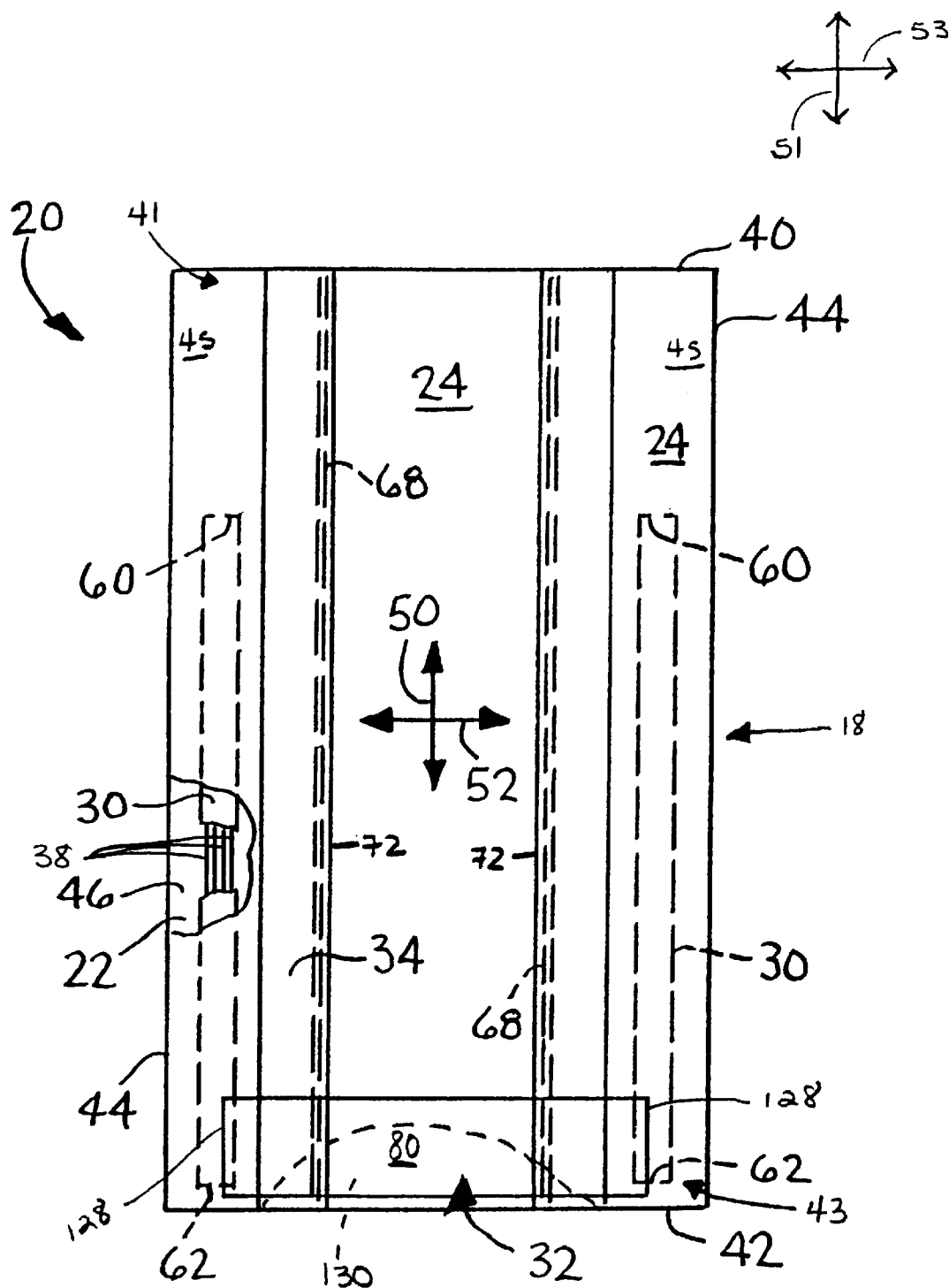
FIG. 3 is a top plan view of the disposable absorbent article shown in FIG. 1, shown in a flat and stretched condition.

One embodiment of a disposable absorbent article 20 according to the present invention is shown in FIGS. 1–3. The absorbent article 20 is specifically designed to address urinary incontinence and be compatible with the adult male anatomy. In general, the absorbent article 20 includes a moisture barrier 22, a bodyside liner 24, and an absorbent assembly 26 (see FIG. 2) sandwiched between the moisture barrier and liner. The absorbent article 20 has a body-conforming cupped region 28 at one end (see FIGS. 1 and 2) as a result of the interaction between two longitudinal gathering members 30 and a transverse gathering member 32 (see FIG. 3). A pair of containment flaps 34 maintain the penis of the wearer in proper position relative to the absorbent article 20 and minimize leakage. An elasticized back pouch member 80 is connected to at least one of the moisture barrier 22 and the bodyside liner 24 along the back end margin 43 of the absorbent article 20. The components of the urinary incontinence absorbent article 20 will now be described in more detail.

The moisture barrier 22 is desirably formed from a flexible, gatherable material that is substantially liquid impermeable. The moisture barrier 22 has a front end 40, a back end 42 longitudinally spaced from the front end 40, and a pair of side edges 44 extending between the front and back ends 40 and 42. The pair of side edges 44 define the outer edges of a pair of laterally opposed side margins 45. The moisture barrier 22 also has opposite major surfaces designated inner surface 46 and outer surface 48.

The elasticized back pouch member 80 in connected to at least one of the moisture barrier 22 and the bodyside liner 24 along the back end margin 43 of the article 20. The shown back pouch member 80 includes an extending flange section 82 and an extending pouch section 84.

The pouch section 84 (see FIGS. 8 and 9) of the back pouch member 80 includes a substantially fixed edge portion 102 secured to the article 20, and includes an elasticized, gathered moveable edge portion 104 which is longitudinally spaced from the fixed edge portion 102. The pouch section 84 also includes a substantially liquid impermeable pouch barrier layer 106, and a pouch fabric layer 108 connected in facing relation with the pouch barrier layer 106. A plurality of separate, laterally extending pouch elastic members 110 are sandwiched between the pouch barrier layer 106 and the pouch fabric layer 108 to provide an elasticized back pouch composite 112 which is substantially laterally gathered.

For the absorbent article 20 to be worn forward of the perineum, the moisture barrier 22 suitably has a length of from about 18 to about 54 centimeters, desirably from about 25 to about 41 centimeters, and particularly about 37 centimeters. The length of the moisture barrier 22 is measured along the outer surface 48 between the front and back ends 40 and 42, parallel to the longitudinal axis 50 of the absorbent article 20 (see FIG. 3). Where the moisture barrier 22 is gathered, such as by an elastic material, the length is measured with the moisture barrier 22 in a generally flat and stretched condition.

FIG. 3 is a representative plan view of the article 20 of the present invention in its flat-out, uncontracted state (i.e. with all elastic induced gathering and contraction removed). Portions of the structure are partially cut away to more clearly show the interior construction of the article 20, and the surface of the article 20 which contacts the wearer is facing the viewer. The pair of side edges 44 and the front and back ends 40 and 42 define a periphery in which the longitudinally extending pair of laterally opposed side margins are designated 45 and the laterally extending front and back end margins are designated 41 and 43 respectively.

The guard 21 typically includes a porous, liquid permeable bodyside liner 24; a substantially liquid impermeable moisture barrier 22; an absorbent assembly 26, positioned and connected between the bodyside liner 22 and the moisture barrier 22; a surge management portion 27; and longitudinal elastic gathering members 30, such as leg elastics members 38. The surge management portion 27 is positioned in liquid communication with the absorbent assembly 26. The absorbent assembly 26 may include a liquid storage layer 56. The bodyside liner 24, moisture barrier 22, absorbent assembly 26, surge management portion 27, and the longitudinal elastic gathering members 30 may be assembled in a variety of well-known male configurations. In addition, the guard 21 may include a pair of containment flaps 34.

As representatively shown, the bodyside liner 24 and the moisture barrier 22 may be generally coextensive, and may have length and width dimensions which are generally larger that the corresponding dimensions of the absorbent assembly 26. The bodyside liner 24 is associated with and superimposed on the moisture barrier 22, thereby defining the periphery of the absorbent article 20. As used herein, the term "associated" encompasses configurations in which the bodyside liner 24 is directly joined to the moisture barrier 22 by affixing the bodyside liner 24 directly to the moisture barrier 22, and configuration wherein the bodyside liner 24 is joined to the moisture barrier 22 by affixing the bodyside liner 24 to intermediate members which in turn are affixed to the moisture barrier 22. The bodyside liner 24 and the moisture barrier 22 can be affixed directly to each other in selected regions, such as in areas along the periphery of the absorbent article 20, by attachment means (not shown), such as adhesive, sonic bonds, thermal bonds, or any other attachment means known in the art. For example, a uniform continuous layer of adhesive, a patterned layer of adhesive, a sprayed pattern of adhesive, or an array of separate lines, swirls, or spots of construction adhesive may be used to affix the bodyside layer 24 to the moisture barrier 22. It should be readily appreciated that the above-described attachment means may also be employed to interconnect and assemble together the various other component parts of the absorbent article 20 described herein.

The moisture barrier 22 suitably has a width in the range of from about 10 to about 25 centimeters, and particularly about 20 centimeters. The width of the moisture barrier 22 is measured along the outer surface 48 between the side edges 44, parallel to the transverse axis 52 of the absorbent article 20.

Where the moisture barrier 22 is gathered, the width is measured in a generally flat and stretched condition. The width of the moisture barrier 22 may but need not narrow toward the back end 42. Regardless of the width of the moisture barrier 22, however, the Resulting Width of the absorbent article 20 desirably narrows toward the back end 42, as described in greater detail below.

In various embodiments of the invention, the selected absorbent assembly 26 is positioned and operably secured between the bodyside liner 24 and the moisture barrier 22. The absorbent assembly 26 has a construction which is generally compressible, conformable, non-irritating to the wearer's skin, and capable of absorbing and retaining liquid body exudates. It should be understood that, for purposes of this invention, the absorbent assembly 26 may comprise a single integral piece of material, or alternatively, may comprise a plurality of individual separate pieces of material which are operably assembled together. Where the absorbent assembly 26 comprises a single, substantially integral piece of material, the material could include the desired structural features formed into selected spatial regions thereof. Where the absorbent assembly 26 comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent assembly 26. Preferably, each piece is connected to an adjacent portion of the absorbent assembly 26 by a suitable bonding and/or fiber entanglement mechanism, such as ultrasonic or adhesive bonding, or mechanical or hydraulic needling.

The absorbent assembly 26 (see FIG. 2) is disposed on the inner surface 46 of the moisture barrier 22 and is desirably sufficiently flexible to readily conform to the contour of the inner surface. The absorbent assembly 26 may be bonded to the inner surface 46 using adhesives or other suitable means.

The absorbent assembly 26 is sized to be shorter and narrower than the moisture barrier 22, and may be manufactured in a wide variety of sizes and shapes including T-shaped, I-shaped, rectangular, hourglass-shaped, or irregularly-shaped.

By way of example, the absorbent assembly 26 may be rectangular with a length in the range of about 8 to about 36 centimeters, particularly about 30 centimeters, and a width in the range of about 1 to about 19 centimeters, particularly about 11 centimeters.

Various types of wettable, hydrophilic fibrous material can be used to form the component parts of absorbent assembly 26. Examples of suitable fibers includes naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester, or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fibers, or by sheathing the nonwettable, hydrophilic fiber with an hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 27 can be provided by a CAHN, SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

In some embodiments, the absorbent assembly 26 comprises a liquid storage layer 56 formed of a material adapted to absorb and retain urine, and optionally, an acquisition layer 58 (see FIG. 2). The absorbent assembly 26 is generally configured according to the amount of liquid intended to be absorbed, and the absorbent rate and capacity of the assembly components. In particular, the storage layer 56 suitably has a capacity of urine of from about 50 grams to about 500 grams, more specifically from about 150 grams to about 350 grams, most specifically about 280 grams. The urine capacity of the storage layer 56 is its saturated retention capacity, which is a measure of the total absorbent capacity of an absorbent garment, material or structure.

Saturated retention capacity of the liquid storage layer 56 may be determined as follows. The material to be tested, having a moisture content of less than about 7 weight percent, is weighed and submerged in an excess quantity of room temperature (about 23 degrees Celsius) synthetic urine. The material to be tested is allowed to remain submerged for 20 minutes. After 20 minutes, the material is removed from the urine and placed on a Teflon® coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material.

The synthetic urine composition referenced herein comprises 1 gram methyl paraben, 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_47H_2O$), 1.33 grams potassium sulphate ($K_2SO_4$), 1.24 grams tribasic sodium phosphate dodecahydrate ($Na_3PO_412H_2O$), 4.4 grams sodium chloride (NaCl), 3.16 grams potassium chloride (KCl). 8.56 grams of urea ($CO(NH_2)_2$), 0.1 grams Pluronic 10R8 surfactant (a non-ionic surfactant commercially available from BASF-Wyandotte Corporation) and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the fluid retained by the tea bag material. Suitable tea bag material is a heat sealable tea bag material grade 542, commercially available from Kimberly-Clark Corporation. The amount of fluid absorbed by the tea bag material is determined by performing the saturated retention capacity test on an empty tea bag. Testing high-absorbency materials or fibers alone can be accomplished using a sealed pouch of tea bag material.

In one embodiment, the liquid storage layer 56 comprises an airlaid batt of wood pulp fluff and high absorbency materials, as hereinafter described. The liquid storage layer 56 may have a thickness of from about 0.2 to about 1 centimeter, such as about 0.5 centimeter, and a density of from about 0.1 to about 0.3 grams per cubic centimeter, such as about 0.18 grams per cubic centimeter.

The liquid storage layer 56 can comprise a matrix of hydrophilic fibers, such as a web of cellulosic fluff, mixed with particles of high-absorbency material. In particular arrangements, the liquid storage layer 56 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be non-uniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the liquid storage layer 56 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of the particles of the absorbent gelling material may also be used in the liquid storage layer 56.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled ABSORBENT COMPOSITES AND ABSORBENT ARTICLES CONTAINING SAME and filed on Sep. 11, 1991, the disclosure of which is hereby incorporated by reference in a manner that is consistent with the present specification.

In a particular aspect of the invention, the liquid storage layer 56 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. Pat. No. 5,147,343 of S. Kellenberger, granted Sep. 15, 1992 and entitled ABSORBENT PRODUCTS CONTAINING HYDROGELS WITH ABILITY TO SWELL AGAINST PRESSURE; and also published Nov. 2, 1989 as European Patent Application No. EP 0 339 461 A1; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include DOW DRYTECH 2035LD polymer obtained from Dow Chemical Co., a business having offices in Midland, Mich.; or FAVOR SAB 870M polymer available from Stockhausen, Inc., a business having offices in Greensboro, N.C.

The matrix of hydrophilic fibers comprising the liquid storage layer 56 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desirable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 300–900 gsm. Again, such basis weight is particularly desirable in the target zone of the absorbent structure. In certain aspects of the invention, the average composite basis weight is within the range of about 300–800 gsm, and preferably is within the range of about 400–750 gsm to provide desired performance.

To provide the desired thinness dimension to the various configurations of the absorbent article 20 of the invention, the liquid storage layer 56 can be configured with a bulk thickness which is not more than about 0.7 cm. Preferably, the bulk thickness is not more than about 0.6 cm, and more preferably is not more than about 0.6 cm to provide improved benefits. The bulk thickness is determined under a restraining pressure of 0.2 psi (1.38 kPa).

The density of the liquid storage layer 56 or other component of the absorbent article 20 can be calculated from its basis weight and thickness. With respect to guards 21, for example, the weight and thickness are measured on newly unpacked, unfolded and dry guards 21 at a restraining pressure of 0.2 psi (1.38 kPa). However, some measurements are taken on packed, folded and dry guards 21 at a restraining pressure of 0.2 psi (1.38 kPa). Conventional thickness measuring devices may be employed to determine the thickness needed to calculate the density.

In the illustrated embodiments of the invention, the liquid storage layer 56 includes about 4 to about 22 grams of wood pulp fluff, preferably includes about 6 to about 18 grams of fluff and more preferably includes about 7 to about 14 grams of fluff to provide desired benefits. The wood pulp fluff generally provides shape and form to the absorbent article 20, and carries and positions the particles of superabsorbent polymer or other high-absorbency material. The liquid storage layer 56 can contain about 3 to about 12 grams of superabsorbent polymer, and in the shown embodiment, contains about 6 grams of superabsorbent polymer. Sufficient superabsorbent polymer is incorporated into the liquid storage layer 56 to provide an adequate total absorbent capacity of at least about 280 gm of synthetic urine.

The fluff and superabsorbent particles can be selectively placed into desired zones of the liquid storage layer 56. For example, the fluff basis weight may vary across the width dimension of the liquid storage layer 56. Alternatively, relatively larger amounts of fluff may be positioned toward the front end 40 of the absorbent article 20. For example, see U.S. Pat. No. 4,585,448 issued Apr. 29, 1986, to K. Enloe. In addition, the superabsorbent material may have a selected zoned placement to reduce the amount of superabsorbent material located proximate the side and end edges of the liquid storage layer 56. The reduced amounts of superabsorbent material at the edges of the liquid storage layer 56 can improve the containment of the superabsorbent particles within the fibrous fluff matrix of the liquid storage layer 56. The pulsed, zoned placement of the superabsorbent material can, for example, be achieved by the method and apparatus described in U.S. Pat. No. 5,028,224 to C. Pieper et al., entitled APPARATUS FOR INTERMITTENTLY DEPOSITING PARTICULATE MATERIAL IN A SUBSTRATE and issued Jul. 2, 1991, the disclosure of which is hereby incorporated by reference in a manner that is consistent herewith.

In a particular aspect of the invention, absorbent assembly 26 can be generally rectangular-shaped, with the narrowest portion of the crotch section having a width of about 3.5 inches (about 8.9 cm) and the front and back ends 40 and 42 having a width of about 4.5 inches (about 11.4 cm).

The entire absorbent assembly 26, or any individual portion thereof, such as the liquid storage layer 56, can be overwrapped in a hydrophilic high wet-strength envelope web, such as a high wet-strength tissue or a synthetic fibrous web. Such overwrapping web can also increase the in-use integrity of the absorbent assembly 26. The web can be suitably bonded, such as with adhesive, to the absorbent assembly 26 and to other components of the product construction.

Due to the high concentrations of superabsorbent particles, or other high-absorbency material, in the liquid storage layer 56, there can be an increased difficulty with regard to containing the high-absorbency particles within the liquid storage layer 56 and restricting the movement or migration of the superabsorbent onto the bodyside of the guard 21. To improve the containment of the high-absorbency material, the absorbent assembly 26 can include an improved overwrap, such as a wrap sheet 74, placed immediately adjacent and around the liquid storage layer 56. The wrap sheet 74 is preferably a layer of absorbent material which covers the major bodyside and outerside surfaces of the liquid storage layer 56, and preferably encloses substantially all of the peripheral edges of the liquid storage layer 56 to form a substantially complete envelope thereabout. Alternatively, the wrap sheet 74 can provide or act as an absorbent wrap which covers the major bodyside and outerside surfaces of the liquid storage layer 56, and encloses substantially only the lateral side edges of the liquid storage layer 56. Accordingly, both the linear and the inwardly curved portions of the lateral side edges of the wrap sheet 74 would be closed about the liquid storage layer 56. In such an arrangement, however, the end edges of the wrap sheet 74 may not be completely closed around the end edges of the liquid storage layer 56 at the front and back ends 40 and 42 of the absorbent article 20.

The absorbent wrap may comprise a multi-element wrap-sheet 74 which includes a separate bodyside wrap layer and a separate outerside wrap layer, each of which extends past all or some of the peripheral edges of the liquid storage layer 56, as representatively shown in FIG. 1. Such a configuration of the wrap sheet 74 can, for example, facilitate the formation of a substantially complete sealing and closure around the peripheral edges of the liquid storage layer 56. In the front and back ends 40 and 42 of the illustrated guard 21, the absorbent wrap may also be configured to extend an increased distance away from the periphery of the liquid storage layer 56.

The bodyside and outerside layers of wrap sheet 74 may be composed of substantially the same material, or may be composed of different materials. For example, the outerside layer of the wrap sheet 74 may be composed of a relatively lower basis weight material having a relatively high porosity, such as a wet strength cellulosic tissue composed of softwood pulp. The bodyside layer of the wrap sheet 74 may comprise one of the previously described wrap sheet materials which has a relatively low porosity. The low porosity bodyside layer of the wrap sheet 74 can better prevent the migration of superabsorbent particles onto the wearer's skin, and the high porosity, lower basis weight outerside layer of the wrap sheet 74 can help reduce costs and facilitate the processibility of the absorbent assembly 26.

To provide the bonding between the bodyside and outerside portions of absorbent wrap, an adhesive, such as NATIONAL STARCH 72-3723 adhesive, or NATIONAL STARCH 72-3945 adhesive can be printed onto the appointed bonding areas of the absorbent wrap with, for example, a rotogravure-type system. With the alternative arrangements having an absorbent wrap composed of a nonwoven meltblown fibrous web, the peripheral sealing of the bodyside and outerside wrap layers may be accomplished by employing hot calendering to provide a sealed strip region around the periphery of the liquid storage layer 56.

Due to the thinness of the liquid storage layer 56 and the high superabsorbent concentrations within the liquid storage layer 56, the liquid uptake rates of the liquid storage layer 56, by itself, may be too low, or may not be adequately sustained over multiple insults of liquid into the absorbent assembly 26. The addition of a porous, liquid-permeable layer of surge management material, however, can advantageously improve the overall uptake rate of the composite absorbent assembly 26. The surge management portion 27 is typically less hydrophilic than the liquid storage layer 56, and has an operable level of density and basis weight to quickly collect and temporarily hold liquid surges, to transport the liquid from its initial entrance point and to substantially completely release the liquid to other parts of the absorbent assembly 26, particularly the liquid storage layer 56. This configuration can help prevent the liquid from pooling and collecting on the portion of the absorbent article 20 positioned against the wearer's skin, thereby reducing the feeling of wetness by the wearer.

The acquisition layer 58 is superposed on top of and in liquid communication with the liquid storage layer 56. Dots or lines of adhesives, ultrasonic bonds or other suitable means may be employed to bond the acquisition layer 58 to the liquid storage layer 56. The acquisition layer 58 may be generally the same size and shape as the liquid storage layer 56. In most cases, the surge management portion 27 is the acquistion layer 58.

The acquisition layer 58 can be or can contain any suitable material for managing, transporting, accommodating, permitting, or directing rapid and/or sudden flow of urine therethrough and into contact with the liquid storage layer 56. The acquisition layer 58 desirably functions to draw liquid from the bodyside liner 24 and then permit desorption by the liquid storage layer 56. One suitable material for the acquisition layer 58 is a latex bonded polyester, which is available from Sackner Products of Grand Rapids, Michigan under the trade designation SH-66. Other suitable materials are disclosed in U.S. Pat. No. 4,798,603 issued Jan. 17, 1989, to Meyer et al., which is incorporated herein by reference.

Various woven and nonwoven fabrics can be used to construct the surge management portion 27. For example, the surge management portion 27 may be a layer composed of a meltblown or spunbonded web of polyolefin fibers. The surge management portion 27 may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion 27 may be composed of a substantially hydrophobic material, and the hydrophobic material may optionally be treated with a surfactant or otherwise processed to impart a desired level of wettability and hydrophilicity.

The representative guard 21 can include a surge management portion 27 which is arranged in a direct, contacting liquid communication with the adjacent liquid storage layer 56. As representatively shown, the surge management portion 27 may be configured for placement adjacent an outwardly facing, outerside of the bodyside liner 24. Optionally, the surge management portion 27 can be placed adjacent an inwardly facing, bodyside surface of the bodyside liner 24. The shown configuration of the surge management portion 27 is operably connected to the bodyside liner 24 with a conventional pattern of adhesive, such as a swirl adhesive pattern. In addition, the surge management portion 27 can be operably connected to the bodyside layer of wrap sheet 74 with a conventional pattern of adhesive. The amount of adhesive add-on should be sufficient to provide the desired levels of bonding, but should be low enough to avoid excessively restricting the movement of liquid from the bodyside liner 24, through the surge management portion 27 and through the wrap sheet 74.

The liquid storage layer 56 is positioned in liquid communication with the surge management portion 27 to receive liquids released from the surge management portion 27, and to hold and store the liquid. In the shown embodiments, the surge management portion 27 comprises a separate layer which is positioned over another, separate layer comprising the liquid storage layer 56, thereby forming a dual-layer arrangement. The surge management portion 27 serves to quickly collect and temporarily hold discharged liquids, to transport such liquids from the point of initial contact and spread the liquid to other parts of the surge management portion 27, and then to substantially completely release such liquids into the layer or layers comprising the liquid storage layer 56.

The representatively shown configuration of the surge management portion 27 is substantially free of absorbent gelling material. Surge management portion 27 may, however, contain a very small amount of particulate gelling material to help acquire an initial liquid surge, but the amount should not be excessive. When excessive amounts of particulate absorbent gelling material are maintained in the target zone, however, the particles can cause the structure to retain and hold unacceptably high amounts of the liquid. In addition, the transport of liquids away from the target zone to other sections of the absorbent assembly 26, particularly the liquid storage layer 56, can be undesirably impaired.

As mentioned previously, the surge management portion 27 can be a separately formed layer, which lies adjacent the outwardly facing surface of the bodyside liner 24 between the liquid storage layer 56 and the bodyside liner 24. Thus, the surge management portion 27 need not comprise the entire thickness of the absorbent assembly 26. The liquid storage layer 56 can optionally include a recess area which wholly or partially surrounds the surge management portion 27, or the liquid storage layer 56 can be entirely positioned below the surge management portion 27. The arrangement which includes the recess in the liquid storage layer 56 can advantageously increase the area of contact and liquid communication between the liquid storage layer 56 and the surge management portion 27. It should be understood, however, that the surge management portion 27 could optionally be constructed to extend through the entire thickness of the absorbent assembly 26 so that the capillary flow of liquid into the liquid storage layer 56 occurs primarily in a generally sideways (X-Y) direction.

The surge management portion 27 can be of any desired shape consistent with the absorbency requirements of the absorbent assembly 26. Suitable shapes include for example, circular, rectangular, triangular, trapezoidal, oblong, dog-boned, hourglass-shaped, or oval. Preferred shapes of the surge management portion 27 are those that increase the contacting, liquid communicating surface area between the surge management portion 27 and the liquid storage layer 56 so that the relative capillarity difference between the surge management portion 27 and the liquid storage layer 56 can be fully utilized. In certain embodiments, for example, the surge management portion 27 can be generally rectangular-shaped.

In the various configurations of the invention, the surge management portion 27 may extend over the complete length of the liquid storage layer 56, or may extend over only a part of the length of the liquid storage layer 56. Where the surge management portion 27 extends only partially along the length of the liquid storage layer 56, the surge management portion 27 may be selectively positioned anywhere along the absorbent assembly 26. For example, the surge management portion 27 may function more efficiently when it is offset toward the front end 40 of the guard 21 and transversely centered within a front section of the absorbent assembly 26. Thus, the surge management portion 27 can be approximately centered about the longitudinal axis 50 of the absorbent assembly 26, and positioned primarily in a central region of the front section of the absorbent assembly 26.

In other aspects of the invention, the end edges of the surge management portion 27 can be spaced longitudinally inboard from the end edges of the liquid storage layer 56. In particular configurations of the invention, the corresponding, relatively adjacent front end edge of the surge management portion 27 can be spaced a predetermined discrete distance from the front end edge of the liquid storage layer 56.

It has been found that an effective fabric for constructing the surge management portion 27 can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994; and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994; the disclosures of which are hereby incorporated by reference in a manner that is consistent herewith.

In desired configurations of the invention, the surge material can include natural fibers, synthetic fibers, such as synthetic polymer fibers, and combinations thereof. The fabric can, for example, be composed of polyolefin fibers, and in particular configurations the fibers can include bicomponent fibers. For example, polypropylene/polyethylene bicomponent fibers may be employed to form the bicomponent fiber portion of any of the described fabrics. In addition, the bicomponent fibers may be flat crimped or helically crimped.

The bodyside liner 24, which is formed of a substantially liquid permeable material, is positioned to sandwich the absorbent assembly 26 between the bodyside liner 24 and the moisture barrier 22. The bodyside liner 24 and moisture barrier 22 may be bonded together longitudinally and transversely outward from the absorbent assembly 26 using thermal bonds, adhesives, ultrasonic bonds or other suitable means. Alternately, the bodyside liner 24 may be bonded to or about the absorbent assembly 26 (not shown). In either case, the bodyside liner 24 desirably covers at least a portion of the absorbent assembly 26. In an alternate embodiment, the bodyside liner 24 is positioned directly over the storage layer 56 and the acquisition layer 58 is bonded to the surface of the liner 24 that is remote from the storage layer 56 (not shown).

The longitudinal elastic gathering members 30 operate together with the transverse elastic gathering member 32 to form the body conforming cupped region 28 particularly suited for male wearers. The longitudinal elastic gathering members 30 comprise an elastic material operatively joined to the moisture barrier 22 along each side edge 44. As illustrated, each longitudinal elastic gathering member 30 includes a plurality of individual elastic strands stretch bonded between a strip of gatherable nonwoven material and the inner surface 46 of the moisture barrier 22 (see FIG. 3). The longitudinal elastic gathering members 30 when in a relaxed state function to gather the moisture barrier 22 along the side edges 44. The longitudinal elastic gathering members 30 may be operatively joined, for example stretch bonded, directly to the moisture barrier 22, the bodyside liner 24, or both.

Rather than being centered between the front and back ends 40 and 42, the longitudinal elastic gathering members 30 are longitudinally offset toward the back end 42 of the moisture barrier 22. Each longitudinal elastic gathering member 30 has forward and rearward terminal points 60 and 62 respectively, which represent the functional ends of the elastic material (see FIG. 3). The forward and rearward terminal points 60 and 62 may be the physical ends of the elastic material, as illustrated, where the full length of the elastic material causes a gathering of the moisture barrier 22. Alternately, the forward and rearward terminal points 60 and 62 may simply represent the forwardmost and rearwardmost locations at which the elastic material is bonded to the moisture barrier 22 (not shown).

In the illustrated embodiment, the body conforming cupped region 28 is formed between the longitudinal center of the absorbent article 20 and the back end 42, and the region near the front end 40 of the absorbent article 20 is generally ungathered so as to lie flat against the abdomen of the wearer. Accordingly, the forward terminal points 60 are desirably spaced from the front end 40 by at least about 7 centimeters, and particularly at least about 10 centimeters, such as about 11 centimeters. Additionally, the forward terminal points 60 are desirably spaced from the back end 42 by less than about 40 centimeters, and particularly less than about 30 centimeters. At the other end, the rearward terminal points 62 are desirably spaced from the back end 42 of the absorbent article 20 by less than about 8 centimeters, desirably less than about 5 centimeters, and particularly less than about 3 centimeters.

The transverse elastic gathering member 32 comprises an elastic material operatively joined to the moisture barrier 22 along the back end 42 of the absorbent article 20. The transverse elastic gathering member 32 may, for instance, be stretch bonded directly to the moisture barrier 22. The transverse elastic gathering member 32 desirably has a length dimension measuring at least about 10 centimeters, such as from about 13 centimeters to about 20 centimeters having a preferred length dimension of about 17 centimeters, and a width dimension measuring at least about 1 centimeter, such as at least about 3.5 centimeters to about 5 centimeters. As illustrated in FIG. 3, the long dimension is positioned to extend parallel to the transverse axis 52 of the absorbent article 20, such that the moisture barrier 22 is gathered and stretchable along the back end 42.

To facilitate formation of the body conforming cupped region 28, the rearward terminal points 62 of the longitudinal elastic gathering members 30 are desirably located within about 6 centimeters, and particularly within about 2 centimeters, of the transverse elastic gathering member 32. In some embodiments, it may be advantageous to have the rearward terminal points 62 coincide with the longitudinal elastic gathering members 30. The transverse elastic gathering member 32 may also function to provide a barrier to liquid flow past the back end 42 of the absorbent article 20. To promote such an upstanding physical barrier, the absorbent assembly 26 is desirably positioned longitudinally inward from the transverse elastic gathering member 32. The positioning of the transverse elastic gathering member 32 longitudinally between the absorbent assembly 26 and the back end 42 is illustrated in FIG. 2.

The absorbent article 20 may optionally also include a front pouch member 66 (see FIG. 10) operatively joined to the moisture barrier 22 along the front end 40. It is desirable for the front pouch member 66 to provide a reduced amount of transverse gathering force as compared to the transverse gathering member 32, which is located along the back end 42. The description herein of the back pouch member 80 applies to the front pouch member 66. As a result, the absorbent article 20 has a Resulting Width that narrows toward the back end 42. The Resulting Width is the distance measured parallel to the transverse axis 52 between the side edges 44, with the elastic in a relaxed condition. One efficient way of accomplishing this is for the transverse elastic gathering member 32 and front pouch member 66 to be formed of the same material and have the same long dimension length, but for the transverse elastic gathering member 32 to have a width dimension that is greater than that of the front pouch member 66.

The longitudinal elastic gathering members 30 and the transverse elastic gathering member 32 are each illustrated as separate elastic materials that are bonded to the moisture barrier 22. These gathering members 30 and 32 could also be formed by treating, for example heat treating, portions of the moisture barrier 22 to give them elastic properties. The gathering members 30 and 32 could also be formed by pleating, a single elastic material of which the gathering members 30 and 32 are integral portions, or other suitable means.

The pair of containment flaps 34 of the illustrated absorbent article 20 are disposed on the bodyside liner 24 and extend generally the full length of the absorbent article 20. The containment flaps 34 include one or more elastic strands 68 (see FIG. 3) which cause the containment flaps 34 to stand upright relative to the bodyside liner 24. The containment flaps 34 may be attached to the bodyside liner 24 using adhesives, ultrasonic bonds, thermal bonds or other suitable means, or formed from the liner. Desirably, however, the containment flaps 34 are separately formed of a substantially liquid impermeable nonwoven material folded upon itself with the elastic strands 68 enclosed therein and attached to the bodyside liner 24. Containment flaps 34 suitable for use in the present invention may be formed as disclosed in U.S.

Pat. Nos. 4,704,116 issued Nov. 11, 1987, and U.S. Pat. No. 4,846,823 issued Jul. 11, 1989, to Enloe, which are incorporated herein by reference. Other configurations of the containment flaps 34 are described in U.S. patent application Ser. No. 208,816 of R. Everett et al., filed on Mar. 4, 1994 and entilted ABSORBENT ARTICLE HAVING AN IMPROVED SURGE MANAGEMENT, the disclosure of which is hereby incorporated by reference in a manner that is consistent herewith.

Such containment flaps 34 can be attached to bodyside liner 24 along length-wise extending fixed regions, such as fixed edges 64, of the flaps 34. A movable edge 72 of each containment flap 34 includes an elastic strand 68 which can comprise one or more individual strands of elastomeric material. For example, a plurality of elastic strands 68 may be configured in a spatially separated, generally parallel arrangement, and a suitable elastic strand can, for example, be composed of a 470 decitex LYCRA elastomer which is available from E.I. DuPont de Nemours, a business having offices in Wilmington, Del. Alternatively, the elastic strands 68 may be composed of 700 denier GLOSPAN S7 spandex elastomer which is available from Globe Manufacturing, a business having offices in Fall River, Mass. The elastic strand 68 is connected to the movable edge 72 of the containment flap 34 in an elastically contractible condition such that the contraction of the elastic components thereof gathers and shortens the edge of the containment flap 34. As a result, the movable edge 72 of each containment flap 34 tends to position itself in a spaced relation away from the bodyside surfaces of the bodyside liner 24 and/or the surge management portion 27 toward a generally upright and approximately perpendicular configuration, especially in the crotch section 18 of the guard 21. In the shown embodiment, for example, the moveable edge 72 of the containment flap 34 is connected to the elastic strands 68 by partially doubling the flap material back upon itself by a limited amount which is sufficient to enclose the elastic strands 68.

At least a pair of containment flaps 34 are connected to laterally opposed, longitudinally extending regions of the bodyside liner 24, and the connected bodyside liner regions are located generally adjacent to laterally opposed side edge regions of the medial section of the bodyside liner 24. The connected bodyside liner regions are located substantially laterally inboard of the leg elastic members 38 of the absorbent article 20, but may optionally be located outboard of the leg elastic members 38.

In the various configurations of the invention, the desired containment flaps 34, may, for example, be constructed of a fibrous material which is similar to the material comprising the bodyside liner 24, or similar to the material comprising the surge management portion 27. Other conventional materials, such as polymer films, may also be employed. In other aspects of the invention, the containment flaps 34 are constructed of a material which is permeable only to gas, such as ambient air. Alternative configurations of the invention can include containment flaps 34 which are constructed of a material which is resistant to a passage of aqueous liquid, such as urine, therethrough. For example, the containment flaps 34 may be constructed of a spunbond-meltblown-spunbond (SMS) laminate material. In the illustrated embodiment, for example, the containment flaps 34 can be constructed of a SMS material having a basis weight of from 0.6 osy to about 0.85 and more preferred about 0.65 osy. The spunbond layers are composed of polypropylene fibers, and the meltblown layer is composed of meltblown polypropylene fibers.

In the various configurations of the invention where selected materials or components, such as the containment flaps 34, are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

The upstanding containment flaps 34 maintain the penis of the wearer in proper position over the transverse center region of the absorbent article 20 and thus over absorbent assembly 26. Because the back end 42 of the absorbent article 20 resides adjacent the perineum of the wearer, the containment flaps 34 desirably extend longitudinally toward the front end 40 to a position at least about 10 centimeters from the back end 42. This assures that for a wide variety of male sizes the containment flaps 34 will be positioned to maintain the penis over the absorbent assembly 26. The containment flaps 34 also provide a barrier to lateral liquid movement, which is particularly significant at locations longitudinally forward of the forward terminal points 60 of the longitudinal elastic gathering members 30. Additionally, the containment flaps 34 assist in forming a pocket for the scrotum of the wearer in the body conforming cupped region 28 of the absorbent article 20. Consequently, the containment flaps 34 desirably extend longitudinally toward the back end 42 to a position less than about 3 centimeters from the back end, and particularly to the back end 42.

The absorbent article 20 may also include attachment means 94 (see FIG. 2), for example garment attachment adhesive 96 and a strip of release paper 98, to secure the moisture barrier 22 to underclothing of the wearer.

Figure 4:
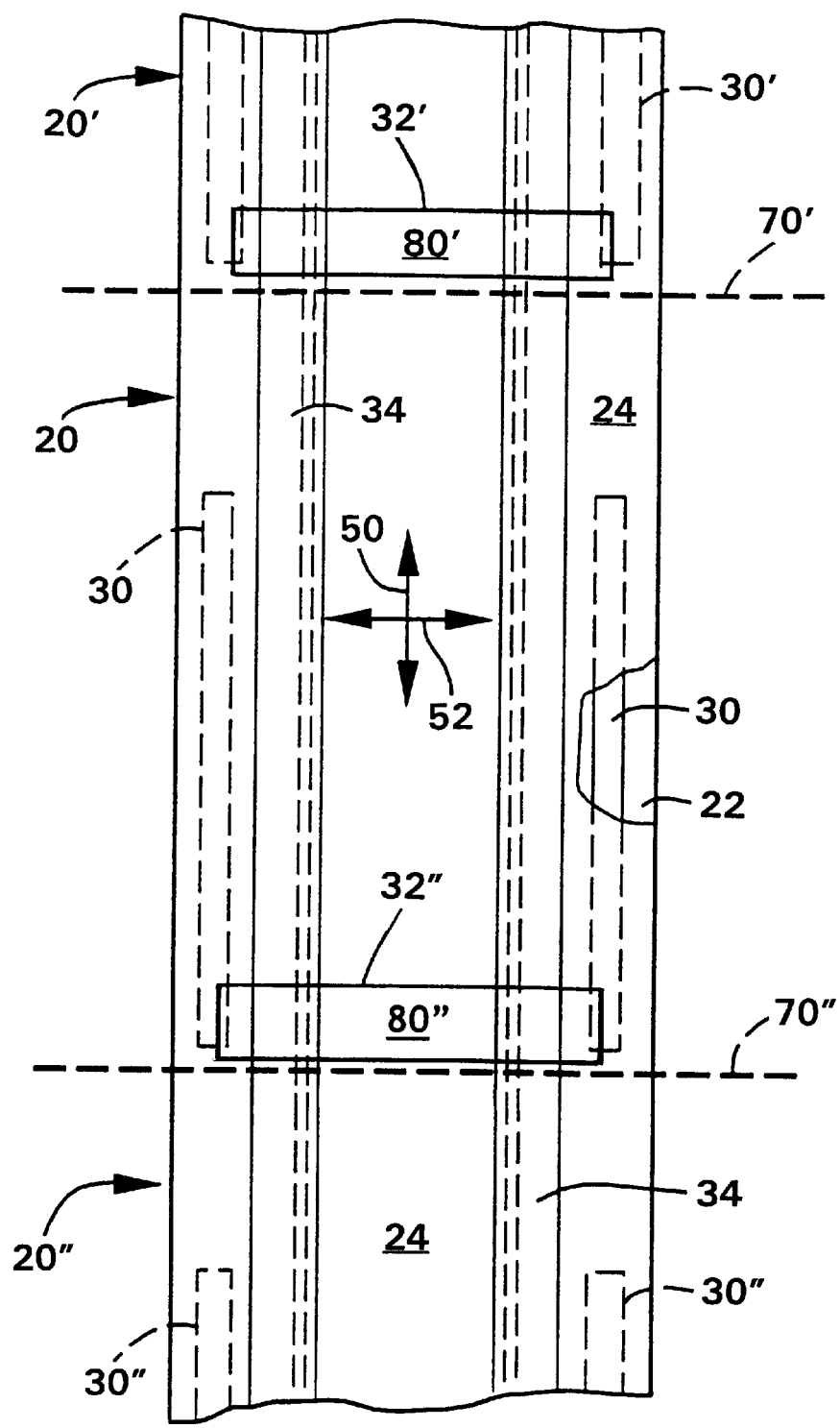
FIG. 4 is a schematic representation of an intermediate stage of assembly of the absorbent articles shown in FIG. 1.

The absorbent article 20 may be constructed by separately forming each element and uniting them as identified above. Alternately, absorbent articles 20 of the invention may be manufactured in a continuous process where the component materials are transported along the machine direction of a manufacturing line, bonded together, and cut to form a series of individual absorbent articles. An assembly of components during a stage of manufacture is illustrated in FIG. 4, where the individual articles are designated 20, 20' and 20".

In the process, a continuous web of moisture barrier material 22 is transported such that the longitudinal axis 50 of each resulting absorbent article is parallel to the machine direction. A continuous web material of the bodyside liner 24 is bonded to the moisture barrier web 22 with a plurality of absorbent assemblies 26 (not shown in FIG. 4) sandwiched between the web of the bodyside liner 24 and the web of the moisture barrier 22.

Additionally, a plurality of longitudinal elastic gathering members 30, 30' and 30" are stretch bonded to the web of the moisture barrier 22. The long dimension of each longitudinal gathering member 30, 30' and 30" is positioned to extend generally parallel to the longitudinal axis of the web of the moisture barrier 22. Alternately, continuous elastic strands or ribbons could be sandwiched between the web of the bodyside liner 24 and moisture barrier 22 and only bonded between the terminal point positions 60 and 62 noted above.

Also, a plurality of transverse elastic gathering members 32' and 32" are stretch bonded to the web of the moisture barrier 22. Each transverse elastic gathering member 32' and 32" defines a long dimension and a width dimension. Each transverse elastic member may be an elasticized back pouch member 80' and 80". The long dimension is positioned to extend parallel to the transverse direction of the web of the moisture barrier 22. The width dimension is thereby positioned to extend parallel to the machine direction of the web of the moisture barrier 22.

The web of the moisture barrier 22, the web of the bodyside liner 24, the longitudinal elastic gathering members 30, 30' and 30", and the transverse elastic gathering members 32' and 32" form an assembly of components that is then transversely cut at spaced locations, such as cutting lines 70' and 70" in FIG. 4. The cutting lines divide the assembly into the individual absorbent articles 20, 20', and 20" and define the front and back ends 40 and 42 of each absorbent article 20, 20', and 20".

Figure 10:
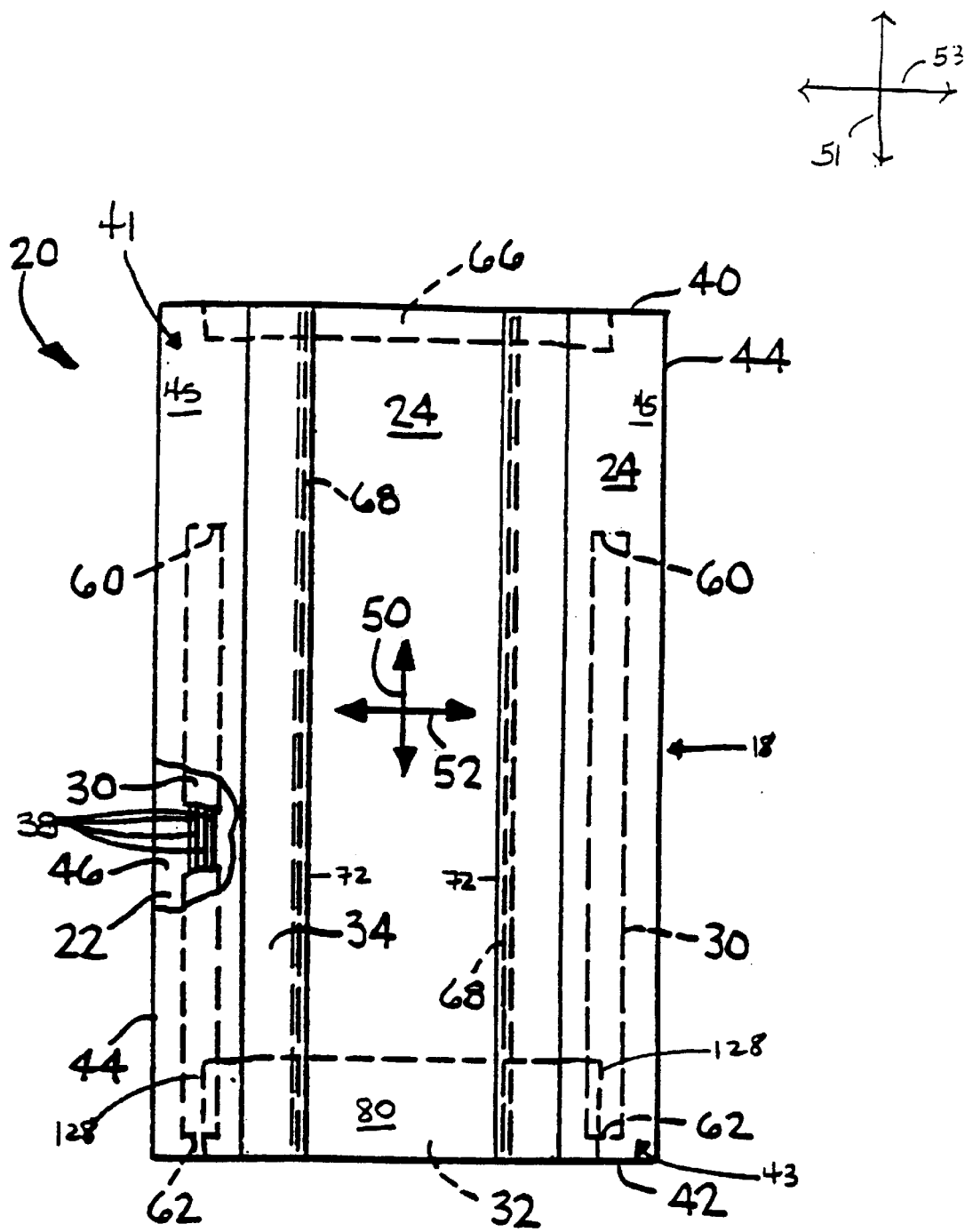
FIG. 10 is a top plan view of the disposable absorbent article showing front and back pouch members in a flat and stretched condition.

The position of the cutting lines 70' and 70" may be readily adjusted to provide each absorbent article 20, 20', and 20" with both a front pouch member 66 and a transverse elastic gathering member 32 as illustrated in FIG. 10. Specifically, the cutting lines 70' and 70" may be spaced to divide each transverse elastic gathering member 32' and 32" into front and back portions, where the back portion of each transverse elastic gathering member 32' and 32" constitutes more than 55 percent, and particularly at least about 75 percent, of the width dimension of the transverse elastic gathering member 32' and 32". The front portion, which forms the front pouch member 66, will provide a reduced amount of transverse gathering force as compared to the back portion, which forms the transverse elastic gathering member 32.

In use, the absorbent article 20 is positioned on the wearer with the front end 40 adjacent the abdomen of the wearer and the back end 42 adjacent the perineum. The scrotum of the wearer tends to reside in the body conforming cupped region 28, due to the cup shape formed by the combination of the longitudinal and transverse elastic gathering members 30 and 32 and the presence of the containment flaps 34 in the body conforming cupped region 28. The penis is located forward of the body conforming cupped region 28 and is maintained over the absorbent assembly 26 by the elasticized containment flaps 34.

With the back end 42 of the article 20 located adjacent the perineum, the wearer can be seated without sitting on a major absorbent portion of the absorbent article 20. This enhances comfort and minimizes compression of the absorbent assembly 26. The transverse elastic gathering member 32 also gives the absorbent article 20 a relatively narrow Resulting Width at the back end 42 so that it can more comfortably fit between the legs of the wearer. At the front end 40, the front region is relatively ungathered compared to the body conforming cupped region 28. This allows the front region to lie relatively flat against the wearer's abdomen, providing a form of discreetness. Urine is quickly absorbed by the absorbent assembly 26, with side leakage minimized by the containment flaps 34.

Figure 5:
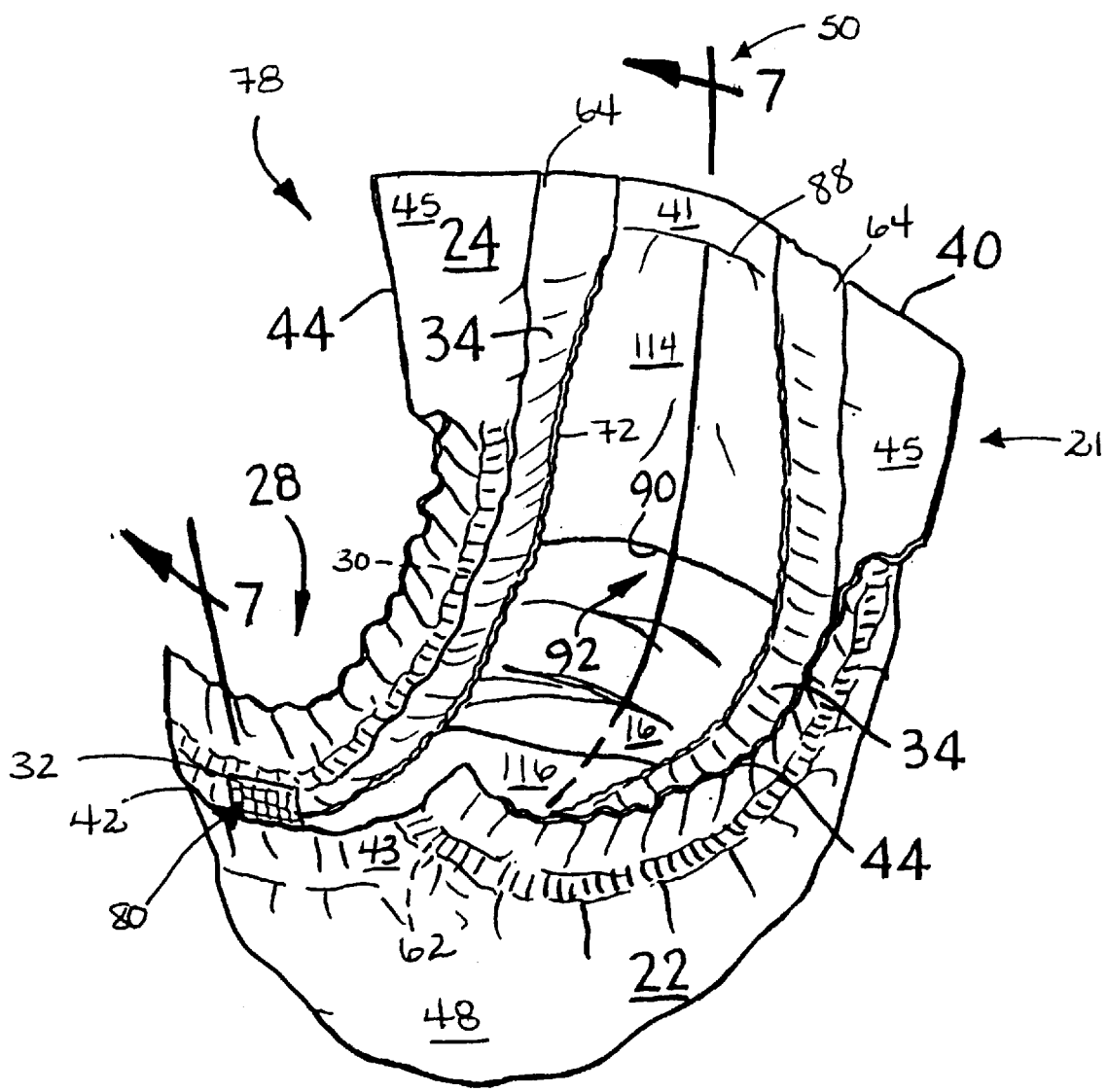
FIG. 5 is a perspective view of an alternate disposable absorbent article according to the present invention.
Figure 6:
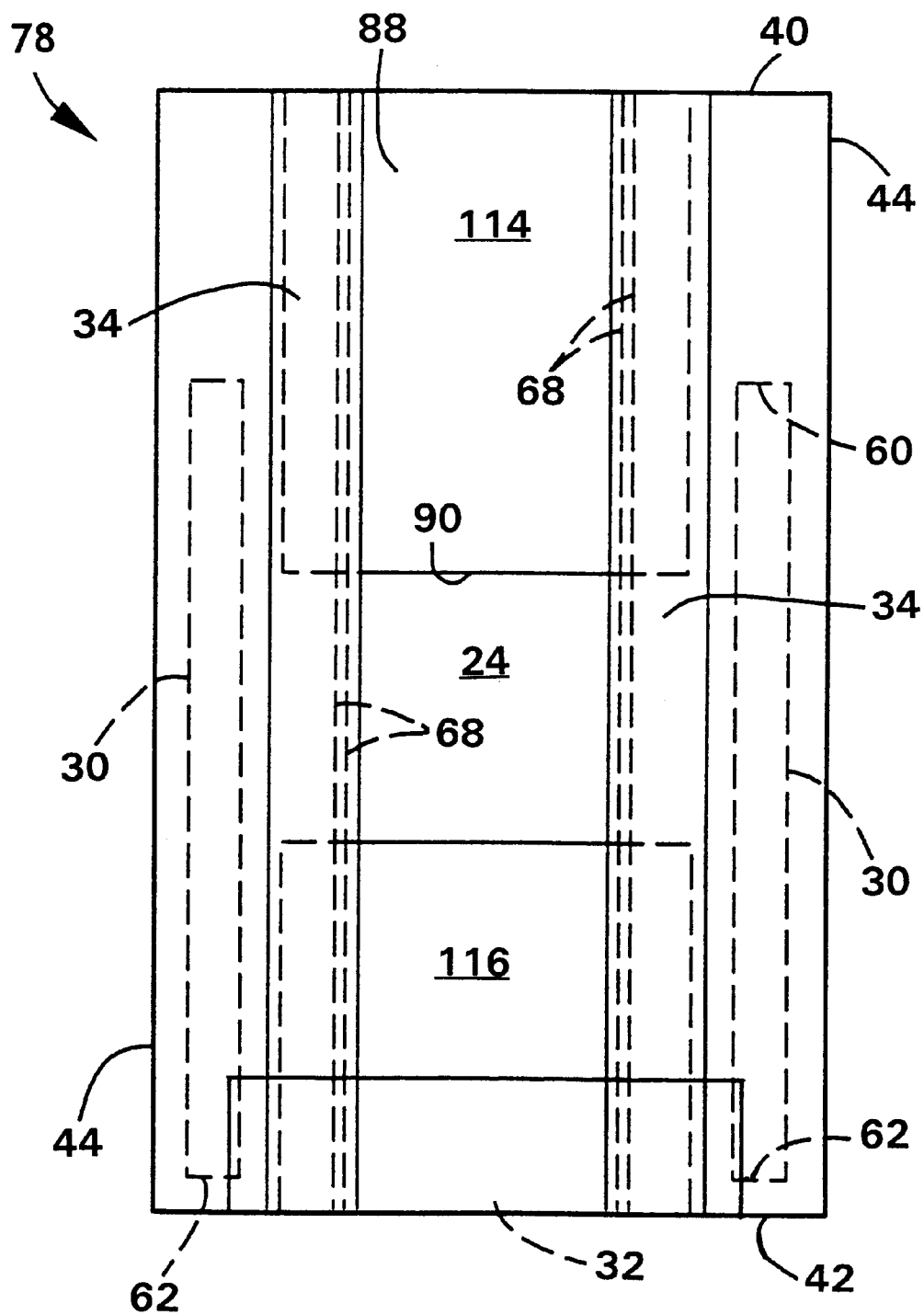
FIG. 6 is a top plan view of the disposable absorbent article shown in FIG. 5, shown in a flat and stretched condition.
Figure 7:
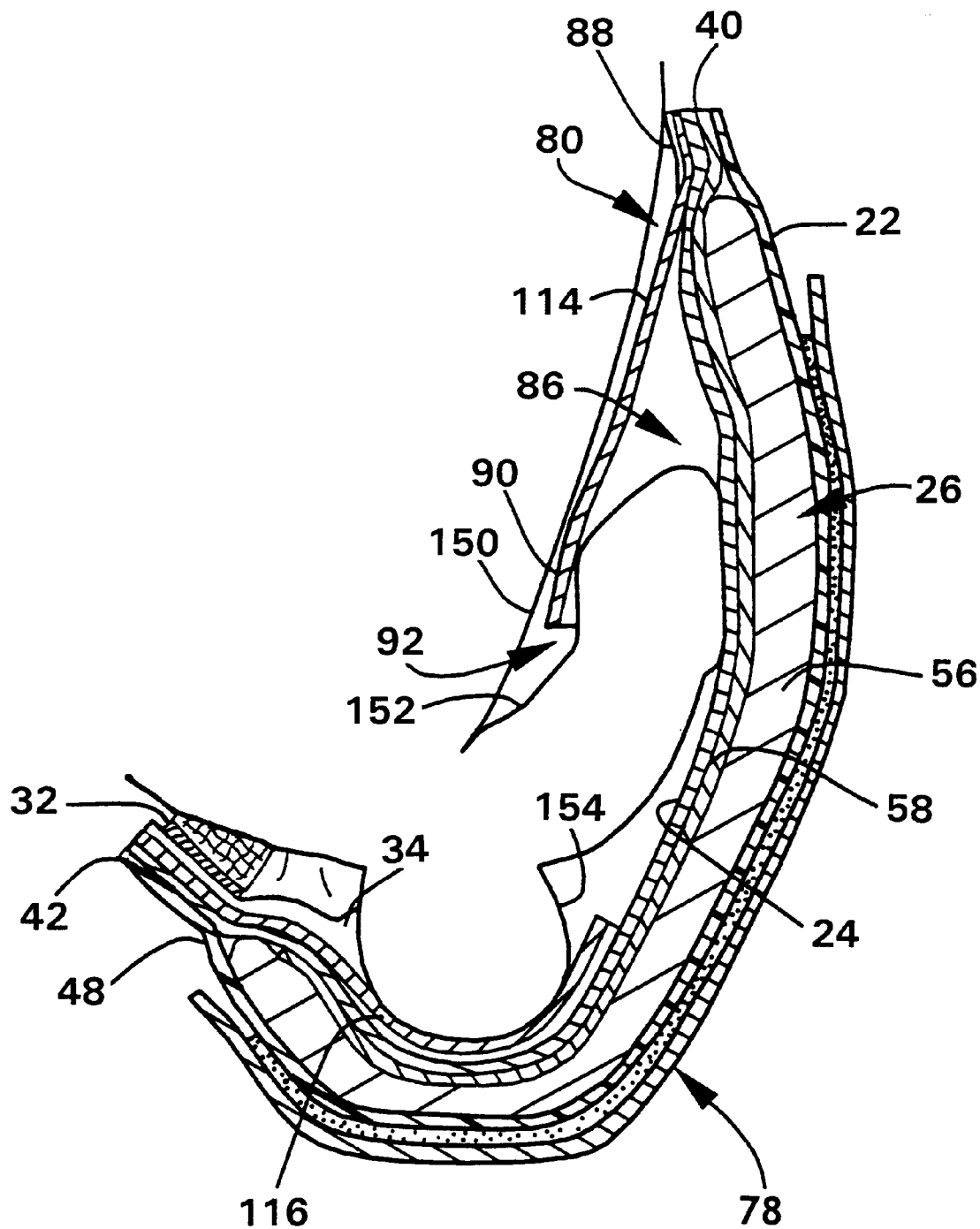
FIG. 7 is an enlarged longitudinal section view taken generally from the plane of the line 7—7 in FIG. 5, and including a representation of the male anatomy while the article is in use.

An alternate absorbent article 78 according to the present invention is illustrated in FIGS. 5–7, where components similar to those previously described have been given the same reference numeral. The absorbent article 78 represents a modification of the absorbent article 20 of FIGS. 1–3 by incorporation of a retaining member 114 and a cover 116. Both the retaining member 114 and cover 116 may be separately formed and bonded to the assembly of components illustrated in FIG. 4 (not shown).

As in the previously-described embodiment, the absorbent article 78 includes a moisture barrier 22 having a front end 40, a back end 42 and side edges 44. A bodyside liner 24 is bonded to the moisture barrier 22 and sandwiches an absorbent assembly 26 (see FIG. 7) between the bodyside liner 24 and moisture barrier 22. The longitudinal elastic gathering members 30 (see FIG. 6) are operatively joined to the moisture barrier 22 along each side edge 44 and desirably offset toward the back end 42. A transverse elastic gathering member 32 (see FIG. 6) is operatively joined to the moisture barrier 22 along the back end 42, and a front pouch member 66 may optionally be provided along the front end 40. The resulting absorbent article 78 has a cupped region 28 toward the back end 42, and may also include a pair of elasticized containment flaps 34.

The retaining member 114 is attached to the bodyside liner 24 such that it defines a compartment 86 (see FIG. 7) for retaining the penis of the wearer in the proper position over the absorbent assembly 26 during use. The retaining member 114 desirably comprises a material that is vapor permeable and liquid impermeable. Suitable materials include films, nonwovens, laminates of films and nonwovens, or the like. For example, the retaining member 114 may be or comprise a cast or blown film formed of polypropylene, polyethylene, or the like, or a gas permeable thermal laminate comprising a polyethylene film and a polypropylene spunbond web.

The retaining member 114 may be generally rectangular in shape with a first end 88, an opposite second end 90, and sides extending between the first and second ends 88 and 90. The first end 88 and the sides are desirably bonded to the bodyside liner 24 using thermal bonds, adhesives, ultrasonic bonds or other suitable means. The second end 90 remains unattached to the bodyside liner 24, however, thereby defining an opening 92 (FIGS. 5 and 7) or point of entry to the compartment 86.

The retaining member 114 is desirably sized so that the sides are positioned adjacent or beneath the containment flaps 34. Further, the first end 88 is desirably positioned adjacent the front end 40. To fit a range of males, the unattached second end 90 and thus the opening 92 are desirably located within about 20 centimeters, more desirably within about 16 centimeters, from the back end 42 of the moisture barrier 22. Further, the retaining member 114 and thus the compartment 86 extend from the opening 92 toward the front end 40 at least about 5 centimeters, desirably at least about 10 centimeters, and more desirably all the way to the front end 40. Accordingly, the retaining member 114 desirably has a surface area of from about 90 to about 210 square centimeters, and particularly about 180 square centimeters.

The compartment 86 represents generally the volume beneath the retaining member 114, such as between the retaining member 114 and the bodyside liner 24, that is available for the penis 152. The compartment 86 may have a volume of from about 25 to about 245 cubic centimeters, particularly about 125 cubic centimeters. The volume of the compartment 86 may be determined by estimating, based on physical measurement, the average dimensions of the compartment 86, or by another suitable method.

The cover 116 is attached to the bodyside liner 24 at the back end 42 of the absorbent article 78 to minimize or prevent leakage from the back end 42 and to keep the scrotum 154 of the wearer dry. The cover 116 may be bonded to the bodyside liner 24 at spaced locations or over its full surface area using thermal bonds, adhesives, ultrasonic bonds or other suitable means. The cover 116 desirably extends longitudinally inward from the back end 42 by at least about 4 centimeters, and particularly about 8 centimeters, and has a surface area of from about 13 to about 194 square centimeters, particularly about 70 square centimeters.

The cover 116 may be formed of a material that is substantially liquid impermeable and vapor permeable. Suitable materials may be or comprise a nonwoven web or cast or blown film formed of polypropylene, polyethylene, or the like, or a gas permeable thermal laminate comprising a polyethylene film and a polypropylene spunbond web.

The absorbent article 78 is illustrated in use in the enlarged longitudinal section view of FIG. 7. The absorbent article 78 is positioned on a male torso 150 such that the front 40 is toward the front of the wearer and the back end 42 is adjacent the perineum. The penis 152 of the wearer is inserted into the opening 92 to reside in the compartment 86, while the scrotum 154 of the wearer resides against the cover 116. In addition to the features and advantages noted above in relation to the embodiment of FIGS. 1–3, the retaining member 114 assists in keeping the absorbent article 78 in a proper position in relation to the penis, both before and during urination without pressing tightly against the skin. The penis is maintained near the absorbent assembly 26, and urine is prevented from escaping by the moisture barrier 22, retaining member 114 and cover 116. In both embodiments, the articles 20 and 78 provide sufficient air flow around the penis 152 and scrotum 154 by not surrounding them with absorbent material. Also, the acquisition layer 58 and the cover 116 (of the absorbent article 78) serve to keep the skin of the wearer dry after urination.

A wide variety of materials may be used to construct the aforementioned components of the absorbent articles 20 and 78. Numerous examples of materials used in constructing absorbent articles 20 are described in the aforementioned U.S. patents incorporated by reference herein.

The moisture barrier 22 desirably comprises a flexible, gatherable material that is substantially liquid impermeable. Such "flexible" materials are compliant and will readily conform to the general shape and contours of the wearer's body. An exemplary material suitable for use in forming the moisture barrier 22 is a thin, substantially liquid impermeable web or sheet of plastic film such as polyethylene, polypropylene, polyvinyl chloride or similar material having a thickness of from about 0.06 mil. to about 2.0 mil. and more preferably about 1.25 mil. Alternately, the moisture barrier 22 may comprise a woven or a nonwoven, fibrous web which has been totally or partially constructed or treated to impart a desired level of liquid impermeability to selected regions of the moisture barrier 22, typically rendering the moisture barrier 22 substantially liquid impermeable. Still alternately, the moisture barrier 22 may comprise a layered or laminated material, such as a thermally bonded plastic film and nonwoven web composite. For example, a clothlike moisture barrier 22 may be composed of an approximately 0.5 osy (about 17.7 g/m$^2$) basis weight, polypropylene spunbond fabric which is laminated and thermally bonded to a stretch-thinned polypropylene film having a thickness of about 0.0006 inch (about 0.015 mm) and a film basis weight of about 14.5 g/m$^2$. The moisture barrier 22 typically provides the outer cover of the absorbent article 20. Optionally, however, the absorbent article 20 may comprise a separate outer cover member 23 which is in addition to the moisture barrier 22.

The moisture barrier 22 may optionally include a microporous, "breathable" material which permits vapors to escape from the absorbent assembly 26 while still preventing liquid exudates from passing through the moisture barrier 22. For example, the breathable moisture barrier 22 may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The moisture barrier 22 can also be embossed or otherwise provided with at matte finish to exhibit a more aesthetically pleasing appearance.

The bodyside liner 24 may be any soft-feeling, compliant, flexible, non-irritating to skin, porous sheet which passes fluids therethrough. The bodyside liner 24 may be less hydrophilic than the material in the absorbent assembly 26. The bodyside liner 24 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton and combinations thereof. The bodyside liner 24 has a pore size that readily allows the passage therethrough of liquids, such as urine and other body exudates. A suitable bodyside liner 24 may also be manufactured from a wide selection of materials, such as porous foams, reticulated foams in addition to the natural and synthetic fibers or combinations of natural and synthetic fibers described above. The bodyside liner 24 may be selectively embossed or perforated with discrete slits or holes extending therethrough, such as an apertured film material.

The bodyside liner 24 may be composed of a substantially hydrophobic and substantially nonwettable material. The hydrophobic material may optionally be treated with a surfactant or otherwise processed to impart a desired level of wettability and hydrophilicity. In a particular embodiment of the invention, the bodyside liner 24 can be a nonwoven, spunbond polypropylene fabric composed of about 2.8 to about 3.2 denier fibers formed into a web having a basis weight of about 20 gsm (g/m$^2$) and density of about 0.13 gm/cc. The fabric can be surface treated with a selected amount of surfactant, such as about 0.28% TRITON X-102 surfactant available from Union Carbide, a business having offices in Danbury, Conn., Base N-62 surfactant from Hodgson Textile Chemical Co., a business having offices in Mountholoy, N.C., or about 0.30% of achovel surfactant available from Hodgson Textile Chemical Company having offices in Mountholoy, N.C. The surfactant can be applied by any conventional means, such as spraying, printing, brush coating, or the like.

The surfactant material, such as a conventional wetting agent, can be applied to a medial section of the bodyside liner 24 to provide a greater wettability of the medial section as compared to a remainder of the bodyside liner 24. In particular configurations, the cross-directional width of the medial section can be substantially equal to or less that the cross-directional width of the surge management portion 27. In alternative configuration, the medial section width can be substantially equal to or less than a cross-directional spacing between a pair of adhesive strips employed to secure the pair of containment flaps 34 onto the bodyside liner 24 and to form a leak resistant barrier seal onto the moisture barrier 22.

The surfactant-treated medial section can be approximately centered with respect to the longitudinal center line or axis 50 of the absorbent article 20, and can extend along substantially the entire length of the bodyside liner 24. Alternatively, the surfactant treated medial section can be constructed to extend along only a pre-determined portion of the length of the bodyside liner 24. One preferred bodyside liner 24 material is a wettable spunbonded polypropylene having a basis weight of about 0.5 ounces per square yard. Such material may be produced by the methods and apparatus described in U.S. Pat. Nos. 4,340,563 and 4,405,297 to Appel et al., which are incorporated herein by reference. The bodyside liner 24 is typically employed to help isolate the wearer's skin from liquids held in the absorbent assembly 26. Various woven fabrics may be used for the bodyside liner 24. The bodyside liner 24 may also be a bonded-carded-web composed of natural and/or synthetic fibers.

The liquid storage layer 56 is desirably an air-formed batt of cellulosic fibers (i.e., wood pulp fluff). One preferred type of wood pulp fluff, which is available under the trade designation CR1654 from Kimberly-Clark Corporation of Neenah, Wis., U.S.A., is a bleached, highly absorbent sulphate wood pulp containing softwood fibers. Optionally, the liquid storage layer 56 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The liquid storage layer 56 may also include compounds to increase its absorbency, such as an effective amount of organic or inorganic high-absorbency materials. For example, the liquid storage layer 56 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst Celanese Corporation, and Allied Colloids, Inc. Typically, the high-absorbency material is capable of absorbing at least about 15 times its weight in water, and preferably is capable of absorbing more than about 25 times its weight in water.

The high-absorbency material can be distributed or otherwise incorporated into the liquid storage layer 56 employing various techniques. For example, the high-absorbency material can be substantially uniformly distributed among the fibers comprising the liquid storage layer 56. The materials can also be nonuniformly distributed within the storage layer fibers to form a generally continuous gradient with either an increasing or decreasing concentration of high-absorbency material, as determined by observing the concentration moving inward from the moisture barrier 22. Alternatively, the high-absorbency material can comprise a discrete layer separate from the fibrous material of the liquid storage layer 56, or can comprise a discrete layer integral with the liquid storage layer 56.

The liquid storage layer 56 may also include a wrap sheet 74 (as described herein) to help maintain the integrity of the fibrous core. This wrap sheet 74 typically comprises a hydrophilic cellulosic material, such as creped wadding or a high wet-strength tissue.

Included among suitable components for acquisition layer 58 are substantially hydrophobic transport materials such as nonwoven polypropylene, polyethylene, polyester, blends thereof, or the like. The acquisition layer 58 may contain or be treated with a suitable surfactant to increase its initial wettability in adjustment of the performance of this invention. When treated with a surfactant, however, the acquisition layer 58 should still be less hydrophilic than the liquid storage layer 56. The presence of an effective amount of surfactant on the acquisition layer 58 can advantageously increase the rate of movement of liquid into the liquid storage layer 56 during initial insult of urine. After the initial insult, however, bodily discharges such as urine will continue to move through the acquisition layer 58 whether or not the surfactant is present therein. Accordingly, the surfactant may be water dispersible, if desired. Various surfactants are available as discussed above.

The acquisition layer 58 may have a substantially uniform density throughout and an essentially or generally nonlayered configuration. The density, for instance, can be from about 0.015 to about 0.5 grams per cubic centimeter, and the thickness can be from about 0.3 to about 1.3 centimeters, such as about 0.6 centimeters. The acquisition layer 58 may have a fiber denier from about 1.5 to about 15, and particularly from about 1.5 to about 6. The acquisition layer 58 may also have a pore size gradient therein, for instance, as having a series of stratified zones, or may have a substantially uniform porosity.

The elastic gathering members 30 and 32 may be formed of a dry-spun coalesced multifilament elastomeric thread sold under the tradename LYCRA and available from I.E. Du Pont de Nemours and Company. Alternately, the elastic gathering members 30 and 32 may be formed of other typical elastics utilized in the diaper-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 22 and the bodyside liner 24. Other suitable elastic gathering means 30 and 32 are disclosed in U.S. Pat. No. 4,938,754 to Mesek and U.S. Pat. No. 4,388,075 to Mesek et al.

The longitudinal elastic gathering members 30 are disposed adjacent the periphery of the guard 21 along each of the pair of side edges 44. The longitudinal elastic gathering members 30 can be connected to either or both of the bodyside liner 24 and the moisture barrier 22 to provide elasticized side margins 45 of the absorbent article 20, and can be arranged to draw and hold the guard 21 against the legs of the wearer to provide elasticized leg bands or leg cuffs. The transverse elastic gathering members 32 is disposed adjacent to the back end 42 of the guard 21 to provide an elasticized back pouch member 80.

The elastic gathering members 30 and 32 are secured to the guard 21 in an elastically contractible condition so that in a normal under strain configuration, the elastic gathering members 30 and 32 effectively contract against the guard 21. The elastic gathering members 30 and 32 can be secured in an elastically contractible condition in a number of ways; for example, the elastic gathering members 30 and 32 may be stretched and secured while the guard 21 is in an uncontracted condition. Alternatively, the guard 21 may be contracted, for example, by pleating, and the elastic gathering members 30 and 32 secured and connected to the guard 21 while the elastic gathering members 30 and 32 are in their relaxed or unstretched condition. Still other means, such as heat-shrink elastic material, may be used to gather the guard 21.

In the embodiment illustrated in FIG. 1, leg elastic members 38 extend essentially along the complete length of the body conforming cupped region 28 of guard 21. Alternatively, the longitudinal elastic gathering members 30 may extend the entire length of the guard 21, or any other length suitable providing the arrangement of elastically contractible lines desired for the particular guard design. The elastic gathering members 30 and 32 may have any of a variety of configurations. For example, the width of the individual longitudinal elastic gathering members 30 may be varied from 0.25 millimeters (0.01 inches) to 25 millimeters (1.0 inches) or more. The longitudinal elastic gathering members 30 may comprise a single strand of elastic material, or may comprise several parallel or non-parallel strands of elastic material, and the elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The longitudinal elastic gathering members 30 may be affixed to the guard 21 in any of several ways which are known in the art. For example, the longitudinal elastic gathering members 30 may be ultrasonically bonded, heat and pressure sealed using a variety of bonding patterns, or adhesively bonded to guard 21 with selected patterns of hotmelt or other type of adhesive. For example, sprayed or swirled adhesive patterns may be employed.

In the illustrated embodiments of the invention, for example, the longitudinal elastic gathering members 30 may comprise a carrier sheet to which are attached a grouped set of elastics composed of a plurality of individual elastic strands. The elastic strands may intersect or be interconnected, or be entirely separated from one another. The shown carrier sheet may, for example, comprise about a 0.67 mil. thick film of untreated polypropylene material. The shown elastic strands can, for example, be composed of LYCRA elastomer which is available from DuPont. Each elastic strand can typically be within the range of about 470–1880 decitex (dtx), and desirably, is about 740 dtx or the equivalent in an embodiment of the invention wherein 3–4 strands are employed for each elasticized legband. Another example of suitable elastic strands can be composed of GLOSPAN elastomer which is available from Globe Manufacturing Co. Each elastic strand can typically be within the range of about 100–1920 denier (den), and desirably, is about 1100 den or the equivalent, in an embodiment of the invention wherein 3–4 strands are employed for each elasticized legband.

In addition, the longitudinal elastic gathering members 30 may be generally straight or optionally curved. For example, the curved longitudinal elastic gathering members 30 can be inwardly bowed toward the longitudinal axis 50 of the guard 21. In particular arrangements, the curvature of the longitudinal elastic gathering members 30 may not be configured or positioned symmetrically relative to the transverse axis 52 of the guard 21. The curved longitudinal elastic gathering members 30 may have an inwardly bowed and outwardly bowed, reflex-type of curvature, and the length-wise center of the longitudinal elastic gathering members 30 may be offset by a selected distance toward either the front or back ends 40 and 42 of the guard 21 to provide desired fit and appearance.

Conventional absorbent articles have incorporated various flap structures at their ends and/or longitudinal side regions. For example, such absorbent articles have typically incorporated a single or multi-layer piece of material, such as polymer films and film-nonwoven laminates, at the end (waistband) portions of the absorbent article along the end in the transverse direction to form a waist flap or dam. The materials, however, typically exhibit similar behavior. When the materials are stretched, they have a tendency to neck down, thereby reducing their effective widths. As they neck down, the materials tend to form relatively large corrugations or furrows which extend substantially along the direction of stretching. The presence of such corrugations can cause the flaps, particularly the flaps in the waist region, to collapse upon themselves, thereby reducing the ability to remain open to receive and trap bodily waste materials. Additionally, when the conventional materials contract, they tend to decrease in overall stiffness, and this decrease in composite stiffness can again allow the flaps to fold over or collapse upon themselves, thereby reducing their effectiveness.

It has been discovered that particular flap structures, such as laminates incorporating individual and separated elastic strands, can provide structures which can overcome the shortcomings of prior structures. When stretched, the elasticized laminates of the back pouch member 80 of the present invention substantially avoid the undesired stretch-wise corrugating effect typically seen across the plane of the conventional flap and along the intended direction of stretch. Desirably, the amount of stretching does not exceed the amount of elongation at which the transverse elastic gathering members 32 are assembled into the laminate. When fully stretched and elongated, the elasticized laminate can lay substantially flat. As the elasticized laminate relaxes and elastically contracts, fine corrugations of sufficient size and frequency can be provided with the furrows or valleys of the corrugate generally aligned to extend substantially perpendicular to the direction of the contraction. The fine corrugations can enhance the stiffness of the structure of the back pouch member 80 and improve its ability to remain open to receive waste materials. The elasticized laminates of the present invention substantially avoid necking when stretched. Additionally, the geometry of the elasticized laminates themselves play an important role in the performance of the materials when employed as a barrier dam structure, such as the shown back pouch member 80. The placement of the transverse elastic gathering members 32 can also play a role in the functionality of the various configurations of the laminas.

It has been found, however, that the identifications of conventional types of materials or families of materials have not been adequate for deriving suitable structures of the back pouch member 80 that are sufficiently effective and reliable. It has been discovered that the performance and effectiveness of the back pouch member 80 is dependent upon particular combinations of properties and behavior characteristics of the materials employed to assemble and construct the back pouch member 80. For example, the incorporation of a back pouch member 80 composed of a polyurethane film or film laminate at the back end 42 of the absorbent article 20, and the placement of a back pouch member 80 composed of a SMS (spunbond-meltblown-spunbond) nonwoven fabric laminate at the back end 42 of the absorbent article 20 have not reliably provided a sufficiently effective structure of the back pouch member 80.

It is important to further configure the materials with particular physical properties. One of the desired physical properties is the stiffness of the back pouch member 80, and the desired stiffness can be achieved in a variety of ways. For example, contributing factors include the basis weight of the materials of the back pouch member 80, the stiffness or modulus of the individual components, the presence of adhesive added to laminas within the back pouch member 80, the pattern and distribution of the applied adhesive, the presence of welding or ultrasonic treatments, the number of individual strands of the transverse elastic gathering members 32 employed in the structure of the back pouch member 80, the geometry of the transverse elastic gathering members 32 placement within back pouch member 80, the presence and alignment of corrugations within the back pouch member 80, and the number of layers of components incorporated within the back pouch member 80.

The present invention can provide a distinctive absorbent article 20, such as the guard 21, which has a cross-wise, transverse dimension 53 and a length-wise, longitudinal dimension 51. The representative guard 21, has a front end 40, a back end 42, and an intermediate portion 16 which interconnects the front and back ends 40 and 42. The absorbent article 20 includes a moisture barrier 22 having a transversely extending width and a longitudinally extending length. A porous, liquid permeable bodyside liner 24 has a transversely extending width and a longitudinally extending length, and is connected in superposed relation to the moisture barrier 22. An absorbent structure, such as the absorbent assembly 26, is sandwiched and operably secured between the moisture barrier 22 and the bodyside liner 24.

As representatively shown in FIGS. 1, 2, and 3, the guard 21 can have a back pouch member 80 which can include a transversely and longitudinally extending flange section 82, and a transversely and longitudinally extending pouch section 84. The extending flange section 82 can, for example, be connected to the bodyside surface of the bodyside liner 24. The pouch section 84 of the back pouch member 80 includes a substantially fixed edge portion 102 which is secured to the absorbent article 20 along and immediately adjacent the boundary of the extending flange section 82, and includes an elasticized, gathered moveable edge portion 104, which is longitudinally spaced from the fixed edge portion 102 by a selected distance. The pouch section 84 thereby provides an operable waist dam and waist flap construction. The pouch section 84 also includes a substantially liquid impermeable pouch barrier layer 106, and a pouch fabric layer 108 which is connected in facing relation with the pouch barrier layer 106. The pouch fabric layer 108 may, for example be composed of a woven or nonwoven fabric, and in the shown arrangement, the pouch fabric layer 108 is desirably a nonwoven. A plurality of separate, laterally extending pouch elastic members 110 are sandwiched and operably connected between the pouch barrier layer 106 and the pouch fabric layer 108 to provide an elasticized back pouch composite 112, which is gathered substantially along the cross-wise transverse dimension 53 and is elastically stretchable at least along the transverse direction. The shown arrangement includes pouch elastic members 110 which are aligned substantially parallel to one another, but optionally can include other separated configurations and alignments of the pouch elastic members 110. Desirably, the pouch fabric layer 108 is arranged for placement against the wearer's skin, although the pouch barrier layer 106 may optionally be appointed for placement immediately adjacent the wearer's skin.

In a particular aspect of the invention, the extending flange section 82 of the back pouch member 80 can include a substantially liquid impermeable flange barrier layer 105, and a flange fabric layer 107 which is operably connected and secured in facing relation with the flange barrier layer 105. The flange fabric layer 107 may, for example, be composed of a woven or nonwoven fabric, and in the shown arrangement, and the flange fabric layer 107 is desirably a nonwoven. A plurality of separate, laterally extending flange elastic members 109 are sandwiched and operably connected between the flange barrier layer 105 and the flange fabric layer 107 to provide an elasticized flange composite 111, which is substantially transversely gathered by the flange elastic members 109 and is elastically stretchable at least along the transverse direction 53. The shown arrangement includes flange elastic members 109 which are substantially parallel to one another, but optionally can include other separated configurations of the flange elastic members 109 which may be non-parallel. Desirably, the flange fabric layer 107 is arranged for placement against the wearer's skin, although the flange barrier layer 105 may optionally be appointed for placement immediately adjacent the wearer's skin. Particular configurations of the flange section 82 can be constructed and arranged to be substantially coterminous with its associated back end margin 43 of the absorbent article 20.

In particular configurations of the invention, such as the arrangements shown in FIGS. 2 and 3, the pouch section 84 of the back pouch member 80 can be integrally formed with the flange section 82 of the back pouch member 80. In these arrangements, the pouch barrier layer 106 is integrally formed with the flange barrier layer 105 to provide a combined, flange-pouch barrier layer 124, and the fabric pouch layer 108 is integrally formed with the flange fabric layer 107 to provide a combined flange-pouch fabric layer 125. The representatively shown arrangement, further includes a flange-pouch barrier layer 124 which is substantially coextensive with the flange-pouch fabric layer 125.

In other arrangements of the invention, the flange elastic members 109 in the flange section 82 are spaced from the closest pouch elastic members 110 in the pouch section 84 by a predetermined boundary space 122 which provides a separation distance of at least about 2 mm. In particular aspects, the separation distance provided by the boundary space 122 is at least about 8 mm, and optionally is at least about 16 mm. The distance of the boundary space 122 provides an amount of isolation which effectively permits the flange elastic members 109 to operate substantially separately from the pouch elastic members 110. Accordingly, the gathering provided by the flange elastic members 109 can be substantially separated from the gathering provided by the pouch elastic members 110.

With reference again to FIGS. 2 and 8, another aspect of the invention can include a configuration in which one of the pouch elastic members 110 in the pouch section 84 is located most proximally adjacent to the substantially fixed edge portion 102. In addition, such adjacent pouch elastic members 110 is located between the substantially fixed edge portion 102 and the moveable edge portion 104 of the pouch section 84, and is spaced from the substantially fixed edge portion 102 of the pouch section 84 by a proximal spacing distance 123 which is not less than about 2 mm, and optionally is not less than about 4 mm. In further aspects of the invention the proximal spacing distance 123 is not more than about 13 mm, and optionally is not more than about 8 mm. The proper selection of the spacing distance 123 can help the pouch section 84, particularly the movable edge portion 104, to maintain an open position spaced-away from the bodyside liner 24 of the absorbent article 20. If the distance is too small, the pouch section 84 may not open reliably. If the distance is too great, the pouch section 84 may not adequately resist excessive collapsing.

Figure 8:
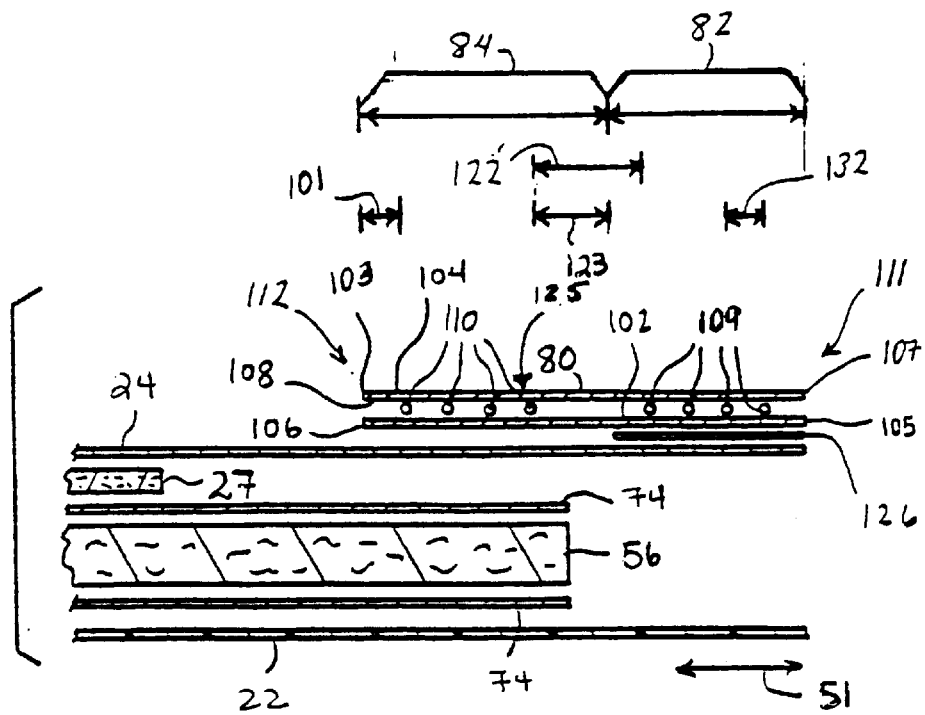
FIG. 8 is an schematic, expanded cross-sectional view of the waist elastic system and the back pouch member of the invention taken generally from the longitudinal plane of the line 2—2 (in FIG. 1) of the article when the pouch section is in its flat-out, uncontracted condition.
Figure 9:
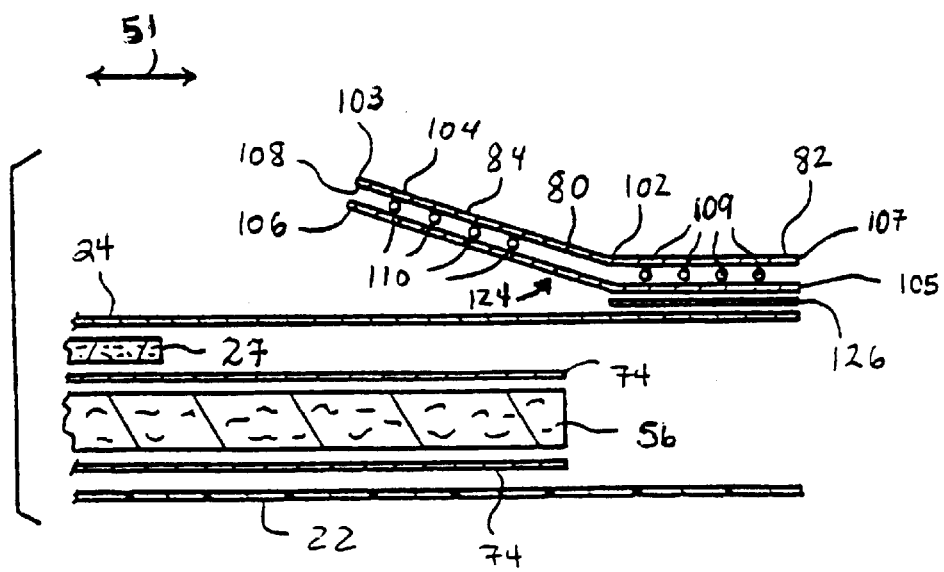
FIG. 9 is an schematic, expanded cross-sectional view of the waist elastic system and the back pouch member of the invention taken generally from the longitudinal plane of the line 2—2 (in FIG. 1) of the article when the pouch section is in its contracted and opened condition.

With reference to FIGS. 8 and 9, the pouch section 84 of the back pouch member 80 can be secured to an appointed region of the absorbent article 20, such as the bodyside liner 24, by a region of attachment 126. In the shown arrangement, the region of attachment 126 extends out of the boundary space 122 to secure the flange section 82 to the bodyside liner 24. Optionally, the region of attachment 126 can be substantially restricted to the boundary space 122, at least within a section of the boundary space 122 which is in a laterally middle or medial portion of the absorbent article 20, and a separate attachment can secure the flange section 82 to the absorbent article 20. Accordingly, the region of attachment 126 can operably provide the substantially fixed edge portion 102 of the pouch section 84. In addition, the pouch section 84 of the back pouch member 80 has laterally opposed end sections 128 which are secured to lie substantially flat against the bodyside liner 24. As a result, the pouch section 84 of the back pouch member 80 can be secured to the bodyside liner 24 with a generally U-shaped arrangement of attachment (see FIGS. 1, 4, and 6).

With reference to FIG. 3, particular configurations of the invention can have the moisture barrier 22 constructed with the back end 42 having an inwardly extending notch region 130 formed therein. The flange section 82 of the back pouch member 80 is configured and arranged to span across the notch region 130. In addition, the longitudinal side edges 44 of the moisture barrier 22 which are located within the back end margin 43 and immediately adjacent the notch section 130 can be operably connected and attached to corresponding portions of the flange section 82.

In the various configurations of the invention, the notch region 130 can have a variety of shapes and sizes. The notch region can have a curvilinear shape, a rectilinear shape, or combinations thereof. Desirably, the waistband notch region 130 can be substantially laterally centered in the cross-directional, medial region of the moisture barrier 22. In the various arrangements of the invention, the cross-directional extent of the notch region 130 is not more than about 80% of the overall, cross-directional extent of the total absorbent article 20, and desirably is not more than about 40% of the overall, cross-directional extent of the absorbent article 20 to provide improved performance. In addition, the cross-directional extent of the notch region 130 can be not less than about 10% of the overall, cross-directional extent of the absorbent article 20, and desirably is not less than about 20% of the overall, cross-directional extent of the absorbent article 20 to provide desired levels of comfort and waste containment. In still other aspects, the longitudinal or depth extent of the notch region 130 is within the range of about 2–15% of the overall longitudinal extent of the total absorbent article 20. In a guard-type absorbent article 20, for example, the notch region 130 can have a maximum, longitudinally inward extent of at least about 9 mm. Alternatively, the inward extent of the notch region 130 is at least about 12.5 mm, and optionally is at least about 15 mm. In other arrangements, the inward extent of the notch region 130 is not more than about 65 mm. Alternatively, the maximum inward extent can be not more than about 55 mm, and optionally can be not more than about 45 mm. When measuring the dimensions of the notch region 130, the absorbent article 20 is placed in its substantially flat-out, uncontracted condition with the elastic gathers at the back end 42 of the absorbent article 20 removed.

With reference to FIGS. 8 and 9, a one of the pouch elastic members 110 is located most proximally adjacent to the terminal edge 103 of the moveable edge portion 104 of the pouch section 84 and is spaced from the terminal edge 103 by a spacing distance 101 of not more than about 13 mm. Alternatively, the edge spacing distance 101 is not more than about 7 mm, and optionally is not more than about 1 mm. In a further aspect, the terminal edge 103 is substantially unfolded. In particular, the terminal edge portion of the pouch section 84 is not folded back upon itself to envelop and enclose one or more of the pouch elastic members 110. The positioning of pouch elastic members 110 proximate the distal, terminal edge 103 can help to maintain the open position of the pouch section 84 across substantially the full width of the pouch section 84. As a result, the pouch section 84 can better provide a functional barrier dam structure.

The various arrangements of the invention can also be constructed to provide the flange and pouch sections 82 and 84, respectively, with desired stiffness values.

In particular, either or both of the flange and pouch sections 82 and 84 can have a stiffness value which is at least about 5 mg. Alternatively, the stiffness can be at least about 15 mg, and optionally, can be at least about 30 mg to provide improved performance. In other aspects of the invention, either or both of the flange and pouch sections 82 and 84 can have a stiffness which is not more than about 250 mg. Alternatively, the stiffness can be not more than about 200 mg, and optionally, can be not more than about 170 mg to provide improved performance. Where the stiffness is too low, the pouch section 84 can be excessively susceptible to collapsing. Where the stiffness is too high, the pouch or flange sections 82 and 84 may cause excessive irritation to the wearer.

The stiffnesses of the flange and pouch sections 82 and 84 of the back pouch member 80 can be determined by employing the test methodology of TAPPI T543 om-94, and by employing a Gurley Digital Stiffness tester, Model 4171-D, a device available from Teledyne Gurley, a business having offices located in Troy, N.Y. The stiffnesses can be expressed as milligrams (mg) which correspond to Standard Gurley Units of milligrams-force. Accordingly, the stiffness values of the various sections of the back pouch member 80 are bending stiffnesses. For the purposes of the present invention, the axis about which a bending moment is applied to the sample during the stiffness testing is a bending axis which Is aligned substantially parallel to the direction of elastic stretch and gathering provided by the associated transverse elastic gathering members 32, such as pouch and flange elastic members 110 and/or 109. With regard to the stiffness testing of the pouch section 84, for example, the bending axis of the test sample of the pouch section 84 would be along an axis line which would have been substantially aligned with the cross-wise transverse dimension 53 of the absorbent article 20, as observed when the pouch section 84 was originally assembled in the absorbent article 20.

In regard to either or both of the flange section 82 and pouch section 84 of the back pouch member 80, the flange and pouch barrier layers 105 and 106 and the flange-pouch barrier layer 124 can be provided by polymer films or fabrics having low permeability to liquid, and combinations thereof. Polymer films may, for example, be composed of polyolefins, polyesters, polyamides and the like. Nonwoven materials can include spunbond-meltblown-spunbond (SMS) fabrics, meltblown fabrics, calendered nonwoven sheets and the like. With respect to the passage of liquid through its thickness, the barrier layers 105, 106, and 124 are constructed to exhibit a hydrohead of resistance which is sufficient to provide an effective barrier against the passage liquids, such as urine.

For example, the barrier layers 105, 106, and 124 may be composed of a 0.0006 inch (0.015 mm) cast, embossed film, such as a CT (XEM400.1), or a 0.0004 inch (0.010 mm) blown film, such as XSF-367, available from Consolidated Thermoplastics, a business having offices located in Chippewa Falls, Wis. The barrier layers 105, 106, and 124 may also be a 0.00035 inch (0.0089 mm) stretch-thinned film, such as XP1024A, available from Edison Plastics a business having offices located in Macalester, Okla. In addition, the barrier layers 105, 106, and 124 may also be a film such as CT (XEM619.2) embossed 0.75 mil polyethylene film, CT (XEM576.2) embossed 0.75 mil polyethylene film, CT(XEM574.2) embossed 0.75 mil polyethylene film, or Huntsman (TSEM 576.2-65) embossed 0.75 mil polyethylene film. Huntsman has office in Chippewa Falls, Wis.

With regard to either or both of the flange section 82 and pouch section 84 of the back pouch member 80, the flange and pouch fabric layers 108 and/or 106 and/or the flange-pouch fabric layer 125 can be composed of a fine denier, low basis weight nonwoven material. Examples of such nonwoven fabrics include polypropylene spunbond materials, bicomponent polypropylene/polyethylene spunbond materials, meltblown materials, SMS materials, through-air-bonded carded webs, point-bonded bonded-carded webs, and the like.

For example, the fabric layers 107, 108, and 125 may comprise a 0.6 osy polypropylene spunbond fabric composed of fibers having denier of less than about 4 den. The fabric layers 107, 108, and 125 can alternatively have fibers with deniers of less than about 3 den, and optionally can include fibers having deniers of less than about 2.5 den.

Either or both of the pouch elastic members 110 and flange elastic members 109 can be composed of strands of natural or synthetic elastomeric materials, such as natural or synthetic rubbers. In particular aspects of the invention, the elastic members can include strands having a denier of not less than about 100 denier. Alternatively, the elastic members 109 and 110 can have a denier of not less than about 180, and optionally can have a denier of not less than about 360. In other aspects of the invention, the elastic members 109 and 110 can include strands having a denier of not more than about 1920 den. Alternatively, the elastic members 109 and 110 can have a denier of not more than about 1140 den, and optionally can have a denier of not more than about 560 den. For example, the pouch elastic members 110 and/or the flange elastic members 109 can include 184 denier GLOSPAN S7 elastic strands available from Globe Manufacturing Co.

To produce the flange and pouch sections 82 and 84 of the back pouch member 80, the pouch elastic members 110 and/or the flange elastic members 109 can be elongated 50–350 percent (as determined with respect to the unstretched length of the elastics) prior to assembly into the back pouch member 80 to form the pouch composite 112 and/or the flange composite 111. For example, the flange elastic members 109 can be configured with about 150 percent elongation to about 200 percent elongation, and the pouch elastic members 110 can have an elongation of about 150 percent to about 200 percent.

The number of strands and the spacing between the strands of the flange and pouch elastic members 109 and 110 can be selected and arranged to provide desired performance. For example, the elastic members 109 and 110 can be selectively configured to provide a desired gasketing function against the wearer's skin while avoiding excessive irritation and redmarking of the wearer's skin.

In particular aspects of the invention, the number of strands of the elastic members 109 and 110 in each of the flange section 82 and/or pouch section 84 can be at least about 2, and alternatively is at least about 3. In further aspects of the invention, the number of elastic strands in each of the elastic members 109 and 110 in each of the flange section 82 and/or pouch section 84 can be not more than about 25. Alternatively, the number of elastic strands in each of the elastic members 109 and 110 in each of the sections 82 and 84 can be not more than about 20, and optionally can be not more than 15. Laminates with too many strands across the longitudinal depth of the pouch section 84 can undesirably cause the pouch structure to lay closed, substantially flat against the bodyside liner 24 of the absorbent article 20, while laminates having too few strands can excessively collapse and fold in upon themselves. The appropriate number of strands, the appropriate spacing between strands, and the appropriate spacing of the strands from the fixed and movable edges of the pouch section 84 are dependent upon the physical properties of the individual laminate components, as well as the dimensions of the pouch section 84.

In other aspects of the invention, the flange elastic members 109 of the flange section 82 and/or pouch section 84 can have an elastic spacing distance 132 which is at least about 2 mm. Alternatively, the elastics spacing distance 132 can be at least about 3 mm, and optionally can be at least about 4 mm. In further aspects, the elastic members of the flange section 82 and/or pouch section 84 can have an elastic spacing distance 132 which not more than about 13 mm. Alternatively, the elastics spacing distance 132 can be not more than about 11 mm, and optionally can be not more than about 8 mm to provide improved control over the operation of the structure of the back pouch member 80.

To further control the operation of the structure of the back pouch member 80, such as the pouch section 84, The pouch elastic members 110 may be uniformly spaced across the entire width of the lamina (as determined along a dimension which is substantially perpendicular to the stretching dimension of the elastic members 110), or they may be grouped into discrete and distinct functional sets. For example, FIG. 9 representatively shows a laminate having more than one functional groupings of the pouch elastic members 110. Such multiple grouping may be placed in either or both of the pouch or flange sections 84 and 82 of the back pouch member 80 to control the operation of the structure of the back pouch member 80 and to enhance performance.

In particular aspects of the invention, the flange elastic members 109 can be arranged to provide for a flange contractive force and the pouch elastic members 110 can be arranged to provide for pouch contractive force. In a particular aspect of the invention, the contractive force exerted by the flange elastic members 109 is configured to be relatively greater than the contractive force exerted by the pouch elastic members 110. The flange elastic members 109 can be longer, or otherwise larger or more strongly contracted, than the pouch elastic members 110. Such an arrangement can provide a desired relative contraction between the flange and pouch sections 82 and 84 of the back pouch member 80 when the back pouch member 80 is operably assembled to the final absorbent article 20, and can help maintain a desired, open condition of the pouch section 84 during use on the wearer.

In a desired aspect of the invention, the elastic members 109 and 110 in the flange section 82, the pouch section 84, respectively, or in both sections 82 and 84 may be operably zone-tensioned, as representatively shown in FIGS. 8 and 9. The zone tensioning may be achieved in a variety of ways. For example, an adhesive or other bonding mechanism may be applied only in the areas where the retraction of the elastic members 109 and 110 is intended to gather the structure of the back pouch member 80. In the regions where the bonds are absent, the remaining elastic members 109 and 110 can contract substantially without gathering the back pouch member 80. Alternatively, other techniques, such as ultrasonics, can be employed to operably deaden the elastic members 109 and 110 in the regions where elastic retraction is not desired.

The elastic members 110 and/or 109 can be attached to either or both of their associated barrier layers 105 and 106 and fabric layers 107 and 108 with a suitable securing means, such as a selected pattern of adhesive or other type of bonding. For example, the adhesive may be applied by spraying adhesive discontinuous droplets or filaments, and/or may be applied by arranging generally continuous lines of adhesive in a selected pattern, such as a swirl pattern. Alternatively, the elastic members 110 and/or 109 can be attached to at least one of the barrier layers 105 and 106 and fabric layers 107 and 108 with a plurality of individual, longitudinally extending strips of adhesive. Each individual adhesive strip is spatially separated from immediately adjacent adhesive strips by a discrete distance, and each individual adhesive strip is arranged to attach substantially an individual one of the elastic members 110 and/or 109 to at least one of the barrier layers 105 and 106 and fabric layers 107 and 108. In the shown arrangements, for example, the strips of adhesive can be aligned substantially parallel to one another.

With reference to FIGS. 8 and 9, the pouch section 84 of the back pouch member 80 may be configured to bridge and span over the inward facing, bodyside surfaces of the longitudinally extending containment flaps 34. Desirably, the movable edge portions 104 of the pouch section 84 are substantially unconnected and unattached to the distal, movable edges 72 of the containment flaps 34 to thereby reduce interaction between the elasticized containment flaps 34 and the elasticized pouch section 84. In addition, it is desirable to zone the elastic tension exerted by the elastic strands 68 employed to elasticize the containment flaps 34. More particularly, the elastic tension in the containment flaps 34 is substantially restricted to a longitudinally medial section of each containment flap 34. Accordingly, the end regions of each containment flap 34, particularly the end regions generally adjacent to the pouch section 84, are substantially free of elastic tension exerted by the elastic strands 68. The distal edges 72 can also be secured to the bodyside liner 24 with a suitable attaching mechanism to further isolate the distal edges 72 of the containment flaps 34 away from the operation and opening of the pouch section 84.

The above-described zoned tensioning of the containment flaps 34 can be achieved in a variety of ways. For example, the elastic contractibility of the elastic strands 68 in the appropriate end regions of the containment flaps can be operably deadened, such as by a mechanical, ultrasonic or thermal treatment which effectively "kills" or otherwise deactivates the elasticity or contractibility in the selected regions. Alternatively, the elastic strands 68 in the end regions of the containment flaps 34 may be substantially unattached to the containment flap material. Accordingly, the elastic strands 68 at the containment flap end regions can elastically retract substantially without exerting a gathering tension onto the end regions of the containment flaps 34. In further configurations, the distal end regions of the containment flaps 34 can be substantially, entirely immobilized, such as by operably securing the end regions onto the bodyside liner 24 with adhesive, sonic bonds or other attaching mechanisms.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. For example, the retaining member 114 or cover 116 could be formed by a portion of the moisture barrier 22 folded over the absorbent assembly 26, or the cover 116 could be formed by a portion of the bodyside liner 24 being treated to be substantially liquid impermeable. Therefore, the invention should not be limited by the specific embodiments described, but only by the claims.

We claim:

1. An absorbent article having a longitudinal axis and a transverse axis, the absorbent article comprising:
   a. a moisture barrier including a liquid impermeable material, the moisture barrier defining a front end, a back end longitudinally spaced from the front end, a pair of side edges extending between the front and back ends, an inner surface and an opposite outer surface, the moisture barrier having a length measured between the front and back ends of less than about 46 centimeters;
   b. an absorbent assembly disposed on the inner surface;
   c. a liner including a liquid permeable material, the liner bonded to the moisture barrier and sandwiching the absorbent assembly therebetween;
   d. means for gathering the moisture barrier along each side edge between forward and rearward terminal points, the forward terminal points spaced from the front end by at least about 7 centimeters and the rearward terminal points spaced from the back end by less than about 5 centimeters;
   e. a pair of elasticized containment flaps disposed on the liner, each containment flap extending longitudinally toward the front end to a position at least about 10 centimeters from the back end;
   f. an elasticized back pouch member connected to at least one of the moisture barrier and the liner along a back end margin of the article, the back pouch member including an extending pouch section and an extending flange section;
      i. the pouch section including
         a substantially fixed edge portion secured to the article,
         an elasticized, gathered moveable edge portion, the moveable edge portion including a terminal edge,
         a substantially liquid impermeable pouch barrier layer,
         a pouch fabric layer connected in facing relation with the pouch barrier layer, and a plurality of separate, laterally extending pouch elastic members sandwiched between the pouch barrier layer and the pouch fabric layer to provide a substantially elasticized back pouch composite which is substantially laterally gathered, the pouch elastic members configured to provide a pouch contractive force;

ii. the flange section including a substantially liquid impermeable flange barrier layer, a flange fabric layer connected in facing relation with the flange barrier layer, and a plurality of separate, laterally extending flange elastic members sandwiched between the flange barrier layer and the flange fabric layer to provide an elasticized flange composite which is substantially laterally gathered by the flange elastic members, the flange elastice members configured to provide a flange contractive force greater than the pouch contractive force; and g. attachment means disposded on the outer surface of the moisture barrier.

2. The absorbent article of claim 1 wherein the pouch section of the back pouch member is integrally formed with the flange section of the back pouch member; the pouch barrier layer is integrally formed with flange barrier layer to provide a flange-pouch barrier layer and the pouch fabric layer is integrally formed with the flange fabric layer to provide a flange-pouch fabric layer.

3. The absorbent article of claim 2 wherein the flange-pouch barrier layer is substantially coextensive with the flange-pouch fabric layer.

4. The absorbent article of claim 2 wherein the flange elastic members are spaced from the pouch elastic members by a boundary space which provides a separation distance of at least about 2 millimeters.

5. The absorbent article of claim 2 wherein the moisture barrier includes a back end edge having an inwardly extending notch region formed therein, and the flange section of the back pouch member is configured to span across the notch region.

6. The absorbent article of claim 1 wherein the pouch elastic members are spaced from the terminal edge of the moveable edge portion of the pouch section by a distance of not more than about 13 millimeters.

7. The absorbent article of claim 1 wherein the pouch section has a bending stiffness of at least about 5 mg which corresponds to Standard Gurley Units of milligrams-force.

8. The absorbent article of claim 1 wherein the pouch section has a bending stiffness of not more than about 250 mg which corresponds to Standard Gurley Units of milligrams-force.

9. The absorbent article of claim 1 wherein the absorbent assembly is positioned longitudinally inward from the back pouch member.

10. An absorbent article having a longitudinal axis and a transverse axis, the absorbent article comprising:

a. a moisture barrier including a liquid impermeable material, the moisture barrier defining a front end, a back end longitudinally spaced from the front end, a pair of side edges extending between the front and back ends, an inner surface and an opposite outer surface, the moisture barrier being generally rectangular and having a length measured between the front and back ends of from about 25 to about 41 centimeters and a width measured between the side edges of from about 10 to about 25 centimeters;

b. an absorbent assembly disposed on the inner surface of the moisture barrier;

c. a liner including a liquid permeable material, the liner bonded to the moisture barrier and sandwiching the absorbent assembly therebetween;

d. longitudinal gathering members operatively joined to the moisture barrier along each side edge, the longitudinal gathering members having forward and rearward terminal points, the forward terminal points spaced from the front end by at least about 7 centimeters and spaced from the back end by less than about 30 centimeters, the rearward terminal points spaced from the back end by less than about 5 centimeters;

e. a pair of elasticized containment flaps disposed on the liner, each containment flap extending longitudinally toward the back end to a position less than about 3 centimeters from the back end and toward the front end to a position at least about 10 centimeters from the back end;

f. an elasticized back pouch member connected to at least one of the moisture barrier and the liner along a back end margin of the article, the back pouch member including an extending pouch section and an extending flange section;

i. the pouch section including a substantially fixed edge portion secured to the article, an elasticized, gathered moveable edge portion, the moveable edge portion including a terminal edge, a substantially liquid impermeable pouch barrier layer, a pouch fabric layer connected in facing relation with the pouch barrier layer, and a plurality of separate, laterally extending pouch elastic members sandwiched between the pouch barrier layer and the pouch fabric layer to provide an elasticized back pouch composite which is substantially laterally gathered, the pouch elastic members configured to provide a pouch contractive force;

ii. the flange section including a substantially liquid impermeable flange barrier layer, a flange fabric layer connected in facing relation with the flange barrier layer, and a plurality of separate, laterally extending flange elastic members sandwiched between the flange barrier layer and the flange fabric layer to provide an elasticized flange composite which is substantially laterally gathered by the flange elastic members, the flange elastice members configured to provide a flange contractive force greater than the pouch contractive force; and g. attachment means disposded on the outer surface of the moisture barrier.

11. The absorbent article of claim 10 wherein the forward terminal points are spaced from the front end by at least about 10 centimeters.

12. The absorbent article of claim 10 wherein pouch section of the back pouch member is integrally formed with flange section of the back pouch member, the pouch barrier layer is integrally formed with the flange barrier layer to form a flange-pouch barrier layer, and the pouch fabric layer is integrally formed with the flange fabric layer to form a flange-pouch fabric layer.

13. The absorbent article of claim 10 wherein the pouch elastic members are spaced from the terminal edge of the moveable edge portion of the pouch section by a distance of not more than about 13 millimeters.

14. The absorbent article of claim 10 wherein the pouch section has a bending stiffness of at least about 5 mg and not more than 250 mg which corresponds to Standard Gurley Units of milligrams-force.

15. The absorbent article of claim 10 wherein the absorbent assembly is positioned longitudinally inward of the back pouch member.

16. An absorbent article having a longitudinal axis and a transverse axis, the absorbent article comprising:
   a. a moisture barrier including a liquid impermeable material, the moisture barrier defining a front end, a back end longitudinally spaced from the front end, a pair of side edges extending between the front and back ends, an inner surface and an opposite outer surface, the moisture barrier having a length measured between the front and back ends of less than about 46 centimeters;
   b. an absorbent assembly disposed on the inner surface;
   c. a liner including a liquid permeable material, the liner bonded to the moisture barrier and sandwiching the absorbent assembly therebetween;
   d. means for gathering the moisture barrier along each side edge between forward and rearward terminal points, the forward terminal points spaced from the front end by at least about 7 centimeters and the rearward terminal points spaced from the back end by less than about 5 centimeters;
   e. a pair of elasticized containment flaps disposed on the liner, each containment flap extending longitudinally toward the front end to a position at least about 10 centimeters from the back end;
   f. an elasticized back pouch member connected to at least one of the moisture barrier and the liner along a back end margin of the article, the back pouch member including an extending pouch section integrally formed with an extending flange section, the integrally formed pouch and flange sections having
      i. a substantially fixed edge portion secured to the article,
      ii. an elasticized, gathered moveable edge portion, the moveable edge portion including a terminal edge,
      iii. a substantially liquid impermeable flange-pouch barrier layer,
      iv. a flange-pouch fabric layer connected in facing relation with the flange-pouch barrier layer,
      v. a plurality of separate, laterally extending pouch elastic members positioned in the pouch section and sandwiched between the flange-pouch barrier layer and the flange-pouch fabric layer to provide a substantially elasticized back pouch composite which is substantially laterally gathered, the pouch elastic members configured to provide a pouch contractive force; and
      vi. a plurality of separate, laterally extending flange elastic members positioned in the flange section and sandwiched between the flange barrier layer and the flange fabric layer to provide an elasticized flange composite which is substantially laterally gathered by the flange elastic members, the flange elastic members configured to provide a flange contractive force greater than the pouch contractive force; and
   g. attachment means disposded on the outer surface of the moisture barrier.

17. The absorbent article of claim 16 wherein flange elastic members are spaced from the pouch elastic members by a boundary space which provides a separation distance of at least about 2 millimeters.

18. The absorbent article of claim 17 wherein the pouch section of the back pouch member is secured to the liner by a region of attachment which is substantially restricted to the boundary space in at least a section of the boundary space which is in a laterally medial portion of the article.

19. The absorbent article of claim 17 wherein the pouch section of the back pouch member has laterally opposed end sections which are secured to lie substantially flat against the liner.

20. The absorbent article of claim 17 wherein the moisture barrier includes a back end edge having an inwardly extending notch region formed therein, and the flange section of the back pouch member is configured to span across the notch region.

* * * * *